United States Patent [19]
Lumma et al.

[11] Patent Number: 5,798,377
[45] Date of Patent: Aug. 25, 1998

[54] THROMBIN INHIBITORS

[75] Inventors: William C. Lumma, Pennsburg; Thomas J. Tucker, North Wales; Keith M. Witherup, Telford; Stephen F. Brady, Philadelphia; Willie L. Whitter, Norristown; Joseph P. Vacca, Telford; Craig Coburn, Skippack; Jules A. Shafer, Gwynedd Valley, all of Pa.

[73] Assignee: Merck & Co., Inc., Rahway, N.J.

[21] Appl. No.: 734,148

[22] Filed: Oct. 21, 1996

[51] Int. Cl.⁶ .................. A61K 31/40; C07D 207/08; C07D 207/09
[52] U.S. Cl. .................. 514/423; 514/425; 548/537; 548/538
[58] Field of Search .................. 514/423, 425; 548/537, 538

[56] References Cited

U.S. PATENT DOCUMENTS

| | | | |
|---|---|---|---|
| 2,277,409 | 3/1942 | Murray | 430/187 |
| 4,346,078 | 8/1982 | Bajusz et al. | 514/19 |
| 4,703,036 | 10/1987 | Bajusz et al. | 514/18 |
| 5,252,566 | 10/1993 | Shuman et al. | 514/210 |
| 5,332,726 | 7/1994 | Klein et al. | 514/18 |
| 5,380,713 | 1/1995 | Balasubramanian et al. | 514/18 |
| 5,416,093 | 5/1995 | Shuman et al. | 514/307 |
| 5,510,369 | 4/1996 | Lumma et al. | 514/422 |

FOREIGN PATENT DOCUMENTS

| | | |
|---|---|---|
| 52881/86 | 1/1986 | Australia . |
| 0 363 284 | 4/1990 | European Pat. Off. . |
| 0 471 651 A2 | 2/1992 | European Pat. Off. . |
| 0 479 489 A2 | 4/1992 | European Pat. Off. . |
| 0 601 459 A2 | 6/1994 | European Pat. Off. . |
| 603112-A1 | 6/1994 | European Pat. Off. . |
| 0 648 780 A1 | 4/1995 | European Pat. Off. . |
| 92/07869 | 5/1992 | WIPO . |
| 92/14750 | 9/1992 | WIPO . |
| 9429336 | 12/1994 | WIPO . |
| 96/31504 | 10/1996 | WIPO . |
| 96/32110 | 10/1996 | WIPO . |

OTHER PUBLICATIONS

Hussain et al., Peptides, "Anticoagulant Activity of a Peptide Boronic Acid Thrombin Inhibitor by Various Routes of Administration in Rats", vol. 12, pp. 1153–1154 (1991).

Vencill et al., Chemical Abstracts, vol. 103, Abstract No. 18900 (1986).

Banner et al., Perspect. Med. Chem., "Chapter 3 —Serine Proteases: 3D Structures, Mechanisms of Action and Inhibitors", pp. 29–43 (1993).

Tapparelli et al., Tips, "Synthetic low–molecular weight thrombin inhibitors: molecular design and pharmacological profile", vol. 14, pp. 366–376, (1993).

Bajusz et al., J. Med. Chem., "Highly Active and Selective Anticoagulants: D–Phe–Pro–Arg–H, a Free Tripeptide Aldehyde Prone to Spontaneous Inactivation and Its Stable N-Methyl Derivative, D–Mephe–Pro–Arg–H", vol. 33, pp. 1729–1735 (1990).

Edwards et al., J. AM. Chem. Soc., "Design, Synthesis, and Kinetic Evaluation of a Unique Class of Elastase Inhibitors, the Peptidyl . . . ", vol. 114, pp. 1854–1863 (1992).

Berndt, M.C. and David R. Phillips, Department of Biochemistry, St. Jude Children's Research Hospital, "Chapter 3 —Platelet membrane proteins: composition and receptor function", pp. 43–75 (1981).

Martin et al., Biochemistry, "Platelet Stimulation by Thrombin and Other Proteases", vol. 14, No. 6, pp. 1308–1314 (1975).

Greco et al., Blood, PPACK-Thrombin Inhibits Thrombin–Induced Platelet Aggregation and Cytoplasmic Acidification but Does Not Inhibit Platelet Shape Change, vol. 75, No. 10, pp. 1983–1990 (1990).

Bode et al., The Embo Journal, "The refined 1.9 Å crystal structure of human a–thrombin: interation with D–Phe–Pro–Arg chloromethylketone and significance of the . . . ", vol. 8, No. 11, pp. 3467–3475 (1989).

Workman et al., The Journal of Biological Chemistry "Structure–Function Relationships in the Interaction of a–Thrombin with Blood Platelets", vol. 252, No. 20, pp. 7118–7123 (1992).

Hui et al., Biochemical and Biophysical Research Communications, "Minimal Sequence Requirement of Thrombin Receptor Agonist Peptide", vol. 184, No. 2, pp. 790–796 (1992).

(List continued on next page.)

*Primary Examiner*—Alan L. Rotman
*Attorney, Agent, or Firm*—Richard S. Parr; Melvin Winokur

[57] ABSTRACT

A compound which inhibits human thrombin and where has the structure

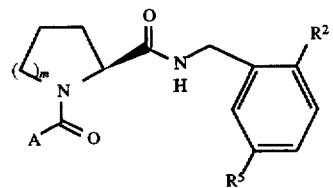

such as

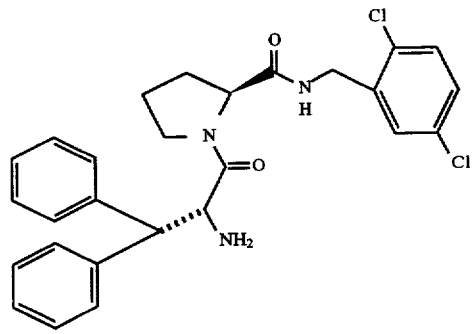

17 Claims, No Drawings

OTHER PUBLICATIONS

Scarborough et al., The Journal of Biological Chemistry, "Tethered Ligand Agonist Peptides Structural Requirements for Thrombin Receptor . . . ", vol. 267, No. 19, pp. 13146–13149 (1992).

Vassallo et al., The Journal of Biological Chemistry, "Structure–Function Relationships in the Activation of Platelet Thrombin Receptors by Receptor–derived Peptides", vol. 267, No. 9, pp. 6081–6085 (1992).

Iwanowicz et al., Organic & Medicinal Chemistry Letters, "a–Hydroxy–and a–Ketoester Functionalized Thrombin Inhibitors", vol. 2, No. 12, pp. 1607–1612 (1992).

Okumura et al., The Journal of Biological Chemistry, "Platelet Glycocalicin–Interaction with Thrombin and Role as Thrombin Receptor of the Platelet Surface", vol. 263, No. 10, pp. 3435–3443 (1978).

Tollefsen et al., The Journal of Biological Chemistry, "The Binding of Thrombin to the Surface of Human Platelets", vol. 249, No. 8, pp. 2646–2651 (1974).

Vu et al., Cell, "Molecular Cloning of a Functional Thrombin Receptor Reveals a Novel Proteolytic Mechanism of Receptor Activation", vol. 64, pp. 1057–1068 (1991).

Gronke et al., The Journal of Biological Chemistry, "Thrombin Interaction with Platelets–Influence of Platelet Protease Nexin", vol. 262, No. 7, pp. 3030–3036 (1987).

Phillips, D. R., Thrombos. Diathes. Haemorrh. (STUTTG.), "Thrombin Interaction with Human Platelets Potentiation of Thrombin–induced Aggregation and Release by Inactivated Thrombin", vol. 32, p. 207 (1974).

Balasubramanian et al., J. Med. Chem., "Active Site–Directed Synthetic Thrombin Inhibitors: Synthesis, in Vitro and in Vivo Activity Profile of BMY 44621 and . . . ", vol. 36, pp. 300–303 (1993).

Kettner et al., The Journal of Biological Chemistry, "The Selective Inhibition of Thrombin by Peptides of Boroarginine", vol. 265, No. 30, pp. 18289–18297 (1990).

Shuman et al., J. Med. Chem., "Highly Selective Tripeptide Thrombin Inhibitors", vol. 36, pp. 314–319 (1993).

THROMBIN INHIBITORS

BACKGROUND OF THE INVENTION

Thrombin is a serine protease present in blood plasma in the form of a precursor, prothrombin. Thrombin plays a central role in the mechanism of blood coagulation by converting the solution plasma protein, fibrinogen, into insoluble fibrin.

Edwards et al., *J. Amer. Chem. Soc.* (1992) vol. 114, pp. 1854–63, describes peptidyl a-ketobenzoxazoles which are reversible inhibitors of the serine proteases human leukocyte elastase and porcine pancreatic elastase.

European Publication 363 284 describes analogs of peptidase substrates in which the nitrogen atom of the scissile amide group of the substrate peptide has been replaced by hydrogen or a substituted carbonyl moiety.

Australian Publication 86245677 also describes peptidase inhibitors having an activated electrophilic ketone moiety such as fluoromethylene ketone or α-keto carboxyl derivatives.

Thrombin inhibitors described in prior publications contain sidechains of arginine and lysine. These structures show low selectivity for thrombin over other trypsin-like enzymes. Some of them show toxicity of hypotension and liver toxicity.

European Publication 601 459 describes sulfonamido heterocyclic thrombin inhibitors, such as N-[4-[(aminoiminomethyl)amino]butyl]-1-[N-(2-naphthalenylsulfonyl)-L-phenylalanyl]-L-prolinamide.

WO 94/29336 describes compounds which are useful as thrombin inhibitors.

SUMMARY OF THE INVENTION

Compounds of the invention have the following structure:

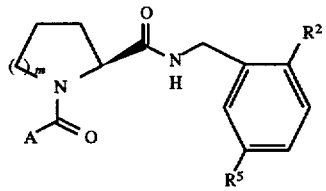

I and pharmaceutically acceptable salts thereof such as

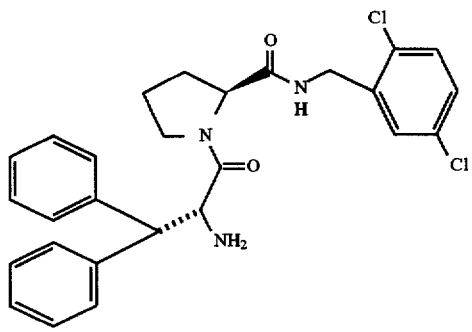

The invention includes a composition for inhibiting loss of blood platelets, inhibiting formation of blood platelet aggregates, inhibiting formation of fibrin, inhibiting thrombus formation, and inhibiting embolus formation in a mammal, comprising a compound of the invention in a pharmaceutically acceptable carrier. These compositions may optionally include anticoagulants (e.g. a fibrinogen receptor antagonist), antiplatelet agents, and thrombolytic agents. The compositions can be added to blood, blood products, or mammalian organs in order to effect the desired inhibitions.

The invention also includes a composition for preventing or treating unstable angina, refractory angina, myocardial infarction, transient ischemic attacks, atrial fibrillation, thrombotic stroke, embolic stroke, deep vein thrombosis, disseminated intravascular coagulation, ocular build up of fibrin, and reocclusion or restenosis of recanalized vessels, in a mammal, comprising a compound of the invention in a pharmaceutically acceptable carrier. These compositions may optionally include anticoagulants (e.g. a fibrinogen receptor antagonist), antiplatelet agents, and thrombolytic agents.

The invention also includes a method for reducing the thrombogenicity of a surface in a mammal by attaching to the surface, either covalently or noncovalently, a compound of the invention.

The use of a compound of claim 1, or a pharmaceutically acceptable salt thereof, in the manufacture of a medicament for inhibiting thrombus formation, preventing thrombus formation, inhibiting thrombin, inhibiting formation of fibrin, and inhibiting formation of blood platelet aggregates, in a mammal

DETAILED DESCRIPTION OF THE INVENTION

Compounds of the invention have the following structure:

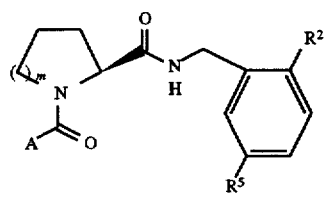

I and pharmaceutically acceptable salts thereof wherein
A is

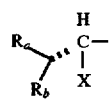

wherein
$R_a$ and $R_b$ are independently selected from
hydrogen,
a heterocyclic group which is a stable 5- to 7-membered mono- or bicyclic or stable 7- to 10-membered bicyclic heterocyclic ring system any ring of which may be saturated or unsaturated, and which consists of carbon atoms and from one to three heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring,
$C_{1-4}$ alkyl unsubstituted or substituted with $CH_3$ or $C_{3-7}$ cycloalkyl,
aryl,
substituted aryl with one or two substituents selected from C$_{1-4}$ alkyl,
C$_{1-4}$ alkoxy,
methylenedioxy,
halogen or
hydroxy,
C$_{3-7}$ cycloalkyl,
a C$_{4-10}$ carbocyclic or bicyclic ring, or
R$_a$ and R$_b$, along with the carbon to which they are attached, form a C$_{3-7}$ cycloalkyl ring or

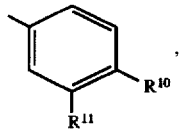

where R$^{10}$ is H or —OH, and
R$^{11}$ is H or —OCH$_3$, and
X is —NHR$_c$ or —OH, wherein,
R$_c$ is
hydrogen,
—CH$_3$,
—(CH$_2$)$_{1-3}$CH$_3$,
—(CH$_2$)$_{2-4}$OH,
—(CH$_2$)$_{1-3}$COOH,
—(CH$_2$)$_{1-3}$COOR$^6$, where R$^6$ is C$_{1-4}$alkyl,
—(CH$_2$)$_{1-3}$CONR$^7$R$^8$,
where R$^7$ and R$^8$ are independently hydrogen or C$_{1-4}$alkyl,

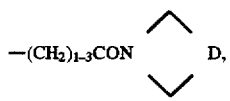

where D is 1, 2, 3, or 4 carbon atoms unsubstituted or any 1, 2, 3, or 4 of which are substituted with OH,
—SO$_2$(CH$_2$)$_{1-3}$aryl,
—(CH$_2$)$_{1-3}$NH$_2$,
C$_{3-7}$ cycloalkyl ring unsubstituted or substituted with —OH, —C(O)OH, or —C(O)OR$_d$, where R$_d$ is C$_{1-4}$ alkyl,

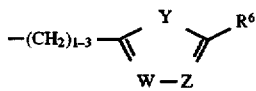

where
Y is O or NH,
W is C or N,
Z is C or N, and
R$^6$ is —CH$_2$OH or —N(CH$_3$)$_2$ provided that W and Z are not the same,

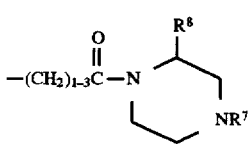

where
R$^7$ is H or CH$_3$, and
R$^8$ is H or

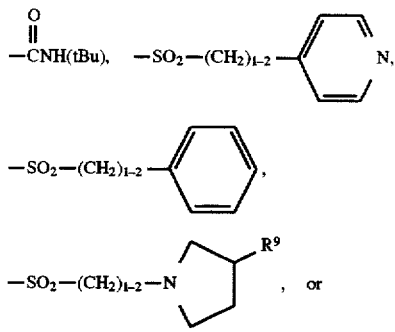

—SO$_2$—(CH$_2$)$_{1-2}$—NH—(CH$_2$)$_2$NH$_2$
where R$^9$ is H, NH$_2$, or OH;
or
A is

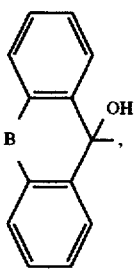

wherein
B is a bond, O, —CH$_2$—O—, or —O—CH$_2$—;
R$^2$ and R$^5$ are independently selected from
hydrogen, provided that R$^2$ and R$^5$ are not both hydrogen,
C$_{1-4}$ alkyl,
C$_{1-4}$ alkoxy,
halogen,
—COOH,
—OH,
—COOR$^6$, where R$^6$ is C$_{1-4}$alkyl,
—CONR$^7$R$^8$, where R$^7$ and R$^8$ are independently hydrogen or C$_{1-4}$alkyl,
—OCH$_2$CO$_2$H,
—OCH$_2$CO$_2$CH$_3$,
—OCH$_2$CO$_2$(CH$_2$)$_{1-3}$CH$_3$,
—O(CH$_2$)$_{1-3}$C(O)NR$^3$R$^4$, wherein R$^3$ and R$^4$ are independently hydrogen, C$_{1-4}$alkyl, C$_{3-7}$ cycloalkyl, or —CH$_2$CF$_3$,
—(CH$_2$)$_{1-4}$OH
—NHC(O)CH$_3$,
—NHC(O)CF$_3$,
—NHSO$_2$CH$_3$, and
—SO$_2$NH$_2$; and m is 1 or 2.

In one class, the compounds have the following structure:

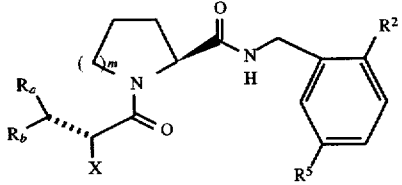

and pharmaceutically acceptable salts thereof wherein

X is as previously defined, $R_a$ and $R_b$ are as previously defined, $R^2$ and $R^5$ are as previously defined, and m is as previously defined.

A first subclass of this class of compounds has the formula

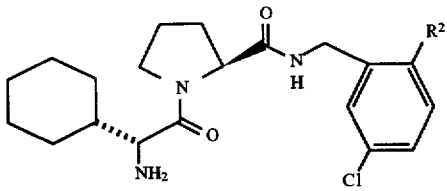

and pharmaceutically acceptable salts thereof, wherein $R^2$ is —OCH$_2$C(O)NHR$^4$; and $R^4$ is —CH$_2$CH$_3$, cyclopropyl, or —CH$_2$CF$_3$.

Examples of compounds in the first subclass include

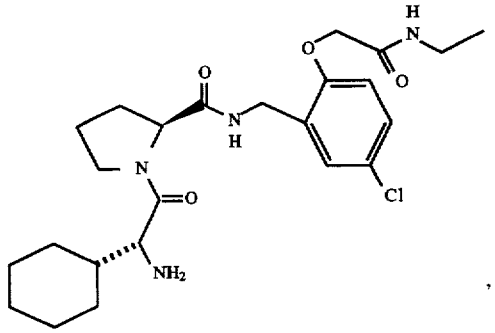

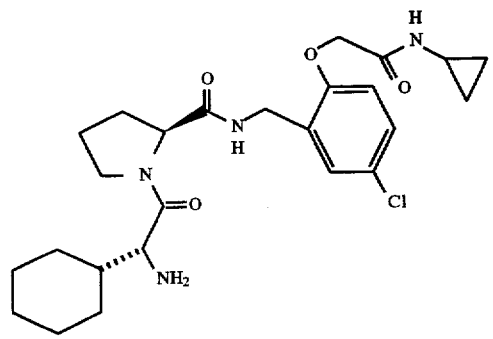

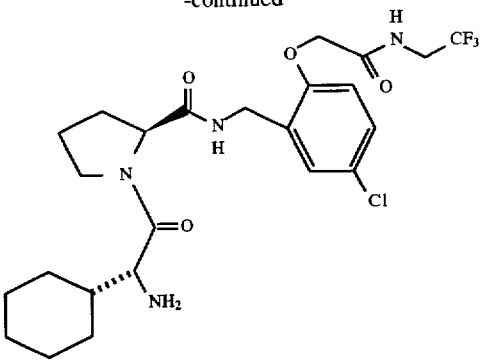

and pharmaceutically acceptable salts thereof.

A second subclass of this class of compounds has the formula

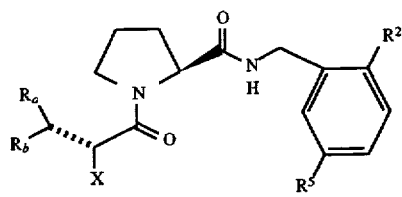

and pharmaceutically acceptable salts thereof wherein

X is —NHR$_c$ or —OH, wherein $R_c$ is
hydrogen,
—CH$_3$,
—(CH$_2$)$_{1-3}$CH$_3$,
—(CH$_2$)$_{2-4}$OH,
—(CH$_2$)$_{1-3}$COOH,
—(CH$_2$)$_{1-3}$COOR$^6$, where R$^6$ is C$_{1-4}$alkyl,
—(CH$_2$)$_{1-3}$CONR$^7$R$^8$, where R$^7$ and R$^8$ are independently hydrogen or C$_{1-4}$alkyl,

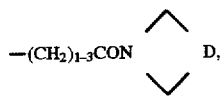

where D is 1, 2, 3, or 4 carbon atoms unsubstituted or any 1, 2, 3, or 4 of which are substituted with OH,
—SO$_2$(CH$_2$)$_{1-3}$aryl,
—(CH$_2$)$_{1-3}$NH$_2$, C$_{3-7}$ cycloalkyl ring unsubstituted or substituted with —OH, —C(O)OH, or —C(O)OR$_d$, where R$_d$ is C$_{1-4}$ alkyl,

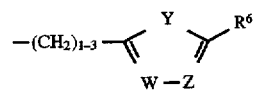

where

Y is O or NH,

W is C or N,

Z is C or N, and

R$^6$ is —CH$_2$OH or —N(CH$_3$)$_2$ provided that W and Z are not the same,

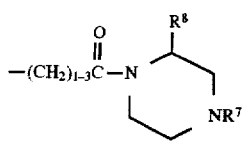

where
R⁷ is H or CH₃, and
R⁸ is H or

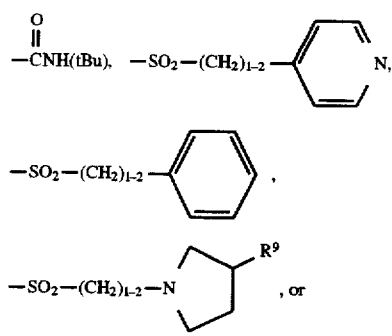

—SO₂—(CH₂)₁₋₂—NH—(CH₂)₂NH₂
where R⁹ is H, NH₂, or OH;
R_a and R_b are as previously defined, and
R² and R⁵ are independently selected from
  hydrogen, provided that R² and R⁵ are not both hydrogen,
  $C_{1-4}$ alkyl,
  $C_{1-4}$ alkoxy,
  halogen, and
  —OH.

A group of this second subclass of compounds has the formula

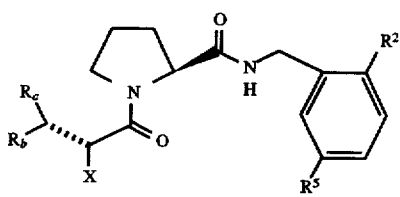

and pharmaceutically acceptable salts thereof wherein
X is as previously defined,
R_a and R_b are independently selected from
  hydrogen,
  a heterocyclic group which is a stable 5- to 7-membered mono- or bicyclic or stable 7- to 10-membered bicyclic heterocyclic ring system any ring of which may be saturated or unsaturated, and which consists of carbon atoms and from one to three heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring,
  $C_{1-4}$ alkyl unsubstituted or substituted with CH₃ or $C_{3-7}$ cycloalkyl,
  phenyl, or R_a and R_b, along with the carbon to which they are attached, form a cyclohexyl ring; and R² and R⁵ are independently selected from
  hydrogen, provided that R² and R⁵ are not both hydrogen,
  Cl,
  —CH₃,
  —CH₂CH₃,
  —OCH₃, and
  —OH.

One subgroup of this group of compounds has the formula

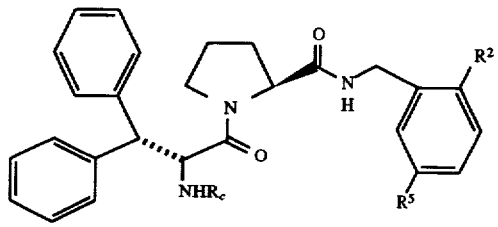

and pharmaceutically acceptable salts thereof wherein

R² and R⁵ are independently selected from —OCH₃ and —CH₃; and

R_c is hydrogen or —SO₂CH₂C₆H₅.

Examples of this subgroup include

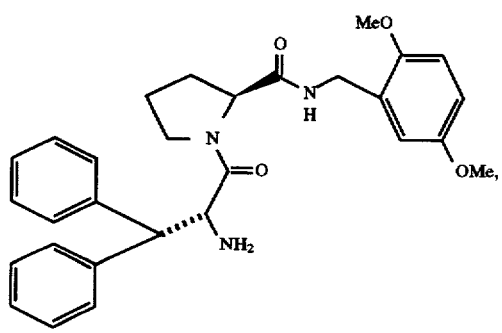

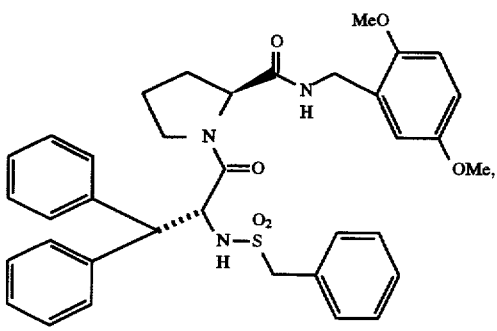

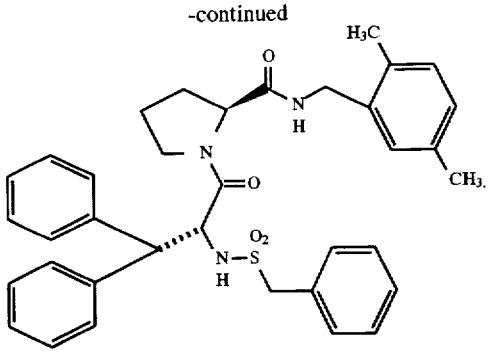

and pharmaceutically acceptable salts thereof.

A second subgroup of this group of compounds has the formula

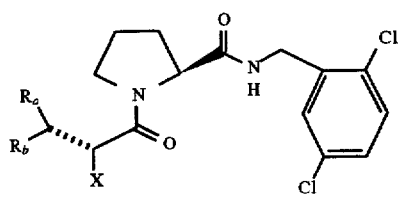

and pharmaceutically acceptable salts thereof wherein

X is as previously defined, and $R_a$ and $R_b$ are as previously defined.

A family of the second subgroup of compounds has the formula

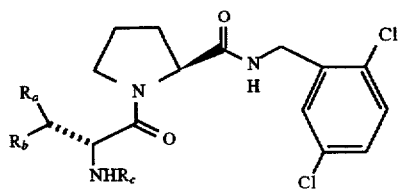

and pharmaceutically acceptable salts thereof, wherein $R_c$ is
  hydrogen,
  $SO_2CH_2C_6H_5$, or

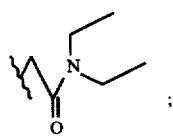

and $R_a$ and $R_b$ are phenyl, or $R_a$ and $R_b$, along with the carbon to which they are attached, form cyclohexyl.

Examples of the family include

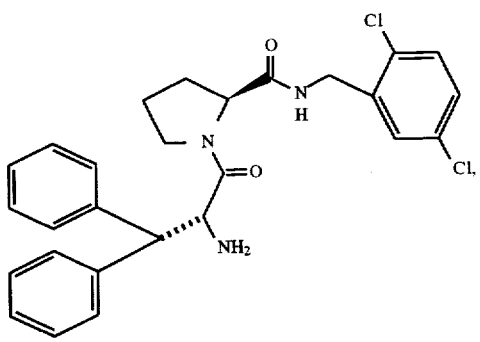

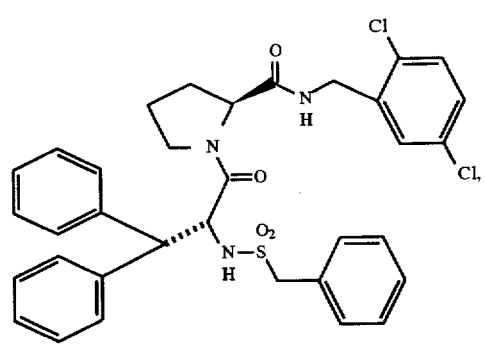

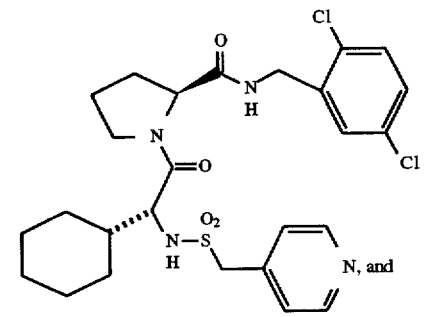

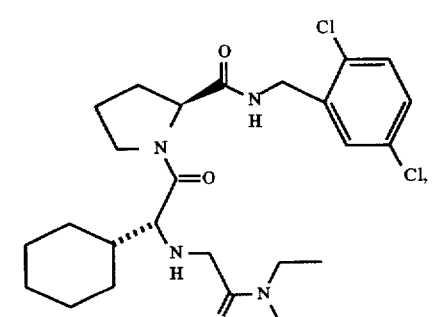

N, and

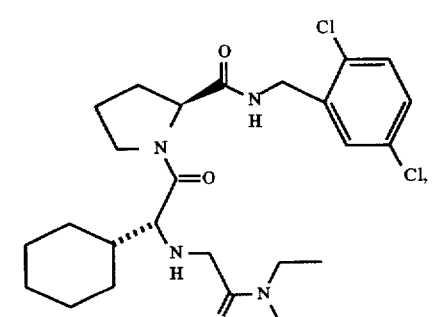

and pharmaceutically acceptable salts thereof.

Some abbreviations that may appear in this application are as follows.

| Designation | |
|---|---|
| BOC(Boc) | t-butyloxycarbonyl |
| HBT(HOBT or HOBt) | 1-hydroxybenzotriazole hydrate |
| BBC reagent | benzotriazolyloxy-bis(pyrrolidino)-carbonium hexafluorophosphate |
| PyCIU | 1,1,3,3-bis(tetramethylene)-chlorouronium hexafluorophosphate |
| EDC | 1-ethyl-3-(3-dimethylaminopropyl) carbodiimide hydrochloride |
| (BOC)₂O | di-t-butyl dicarbonate |
| DMF | dimethylformamide |
| Et₃N or TEA | triethylamine |
| EtOAc | ethyl acetate |
| TFA | trifluoroacetic acid |
| DMAP | dimethylaminopyridine |
| DME | dimethoxyethane |
| BH3-THF | Borane-tetrahydrofuran complex |
| D-Phe(3,4-Cl₂) | D-3,4-Dichlorophenylalanine |
| D-3,3-dicha | D-3,3-Dicyclohexylalanine |
| Pro | Proline |
| Arg | Arginine |
| Gly | Glycine |
| D-3,3,-diphe | D-3,3-Diphenylalanine |

The compounds of the present invention may have chiral centers and occur as racemates, racemic mixtures and as individual diastereomers, or enantiomers with all isomeric forms being included in the present invention.

When any variable occurs more than one time in any constituent or in formula I, its definition on each occurrence is independent of its definition at every other occurrence. Also, combinations of substituents and/or variables are permissible only if such combinations result in stable compounds.

The term "aryl" means a 5- or 6-membered aromatic ring containing 0, 1, or 2 heteroatoms selected from O, N, and S. Examples of aryl include phenyl, pyridine, pyrimidine, imidazole, thiophene, oxazole, isoxazole, thiazole, and amino- and halogen- substituted derivatives thereof.

The term "alkyl" means straight or branched alkane containing 1 to about 10 carbon atoms, e.g., methyl, ethyl, n-propyl, isopropyl, n-butyl, isobutyl, sec-butyl, tert-butyl, pentyl, iso-amyl, hexy, octyl radicals and the like, straight or branched alkene containing 2 to about 10 carbon atoms, e.g., propylenyl, buten-1-yl, isobutenyl, pentenylen-1-yl, 2,2-methylbuten-1-yl, 3-methylbuten-1-yl, hexen-1-yl, hepten-1-yl, and octen-1-yl radicals and the like, or straight or branched alkyne containing 2 to about 10 carbon atoms, e.g., ethynyl, propynyl, butyn-1-yl, butyn-2-yl, pentyn-1-yl, pentyn-2-yl, 3-methylbutyn-1-yl, hexyn-1-yl, hexyn-2-yl, hexyn-3-yl, 3,3-dimethylbutyn-1-yl radicals and the like.

The term "alkoxy" represents an alkyl group of indicated number of carbon atoms attached through an oxygen bridge. Examples of alkoxy include methyloxy, propyloxy, and butyloxy.

The terms "Halo" or "halogen," as used herein, means fluoro, chloro, bromo and iodo.

The term "counterion" is used to represent a small, single negatively-charged species, such as chloride, bromide, hydroxide, acetate, trifluroacetate, perchlorate, nitrate, benzoate, maleate, tartrate, hemitartrate, benzene sulfonate, and the like.

The term heterocycle or heterocyclic, as used herein except where noted, represents a stable 5- to 7-membered mono- or bicyclic or stable 7- to 10-membered bicyclic heterocyclic ring system any ring of which may be saturated or unsaturated, and which consists of carbon atoms and from one to three heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. The heterocyclic ring may be attached at any heteroatom or carbon atom which results in the creation of a stable structure. Examples of such heterocyclic elements include piperidinyl, piperazinyl, 2-oxopiperazinyl, 2-oxopiperidinyl, 2-oxopyrrolodinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isoxazolyl, isoxazolidinyl, morpholinyl, thiazolyl, thiazolidinyl, isothiazolyl, quinuclidinyl, isothiazolidinyl, indolyl, quinolinyl, isoquinolinyl, benzimidazolyl, thiadiazoyl, benzopyranyl, benzothiazolyl, benzoxazolyl, furyl, tetrahydrofuryl, tetrahydropyranyl, thienyl, benzothienyl, thiamorpholinyl, thiamorpholinyl sulfoxide, thiamorpholinyl sulfone, and oxadiazolyl. Morpholino is the same as morpholinyl.

An example of the moiety of $R_a$ or $R_b$ independently selected from substituted aryl with one or two substituents selected from methylenedioxy is

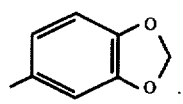

The pharmaceutically-acceptable salts of the compounds of Formula I (in the form of water- or oil-soluble or dispersible products) include the conventional non-toxic salts or the quaternary ammonium salts which are formed, e.g., from inorganic or organic acids or bases. Examples of such acid addition salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate, and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. Also, the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl and diamyl sulfates, long chain halides such as decyl, lauryl, myristyl and stearyl chlorides, bromides and iodides, aralkyl halides like benzyl and phenethyl bromides and others.

Amide couplings used to form the compounds of this invention are typically performed by the carbodiimide method with reagents such as dicyclohexylcarbodiimide, or 1-ethyl-3-(3-dimethylaminopropyl) carbodiimide. Other methods of forming the amide or peptide bond include, but are not limited to the synthetic routes via an acid chloride, azide, mixed anhydride or activated ester. Typically, solution phase amide coupling are performed, but solid-phase synthesis by classical Merrifield techniques may be employed instead. The addition and removal of one or more protecting groups is also typical practice.

Compounds of the invention can be prepared according to the general procedures outlined below:

A protected amino acid such as D-cyclohexylglycine is coupled to proline methyl ester using a coupling agent such as EDC and HOBT. The coupled product is then hydrolyzed with base such as lithium hydroxide, and the resultant acid is coupled to the desired amine such as 2,5-dichlorobenzylamine. The product is treated with a strong acid such as HCl gas or trifluoroacetic acid to remove the t-butyloxycarbonyl protecting group. Tables I and II illustrate compounds synthesized in this manner and are exemplified by Example 1.

SCHEME 1

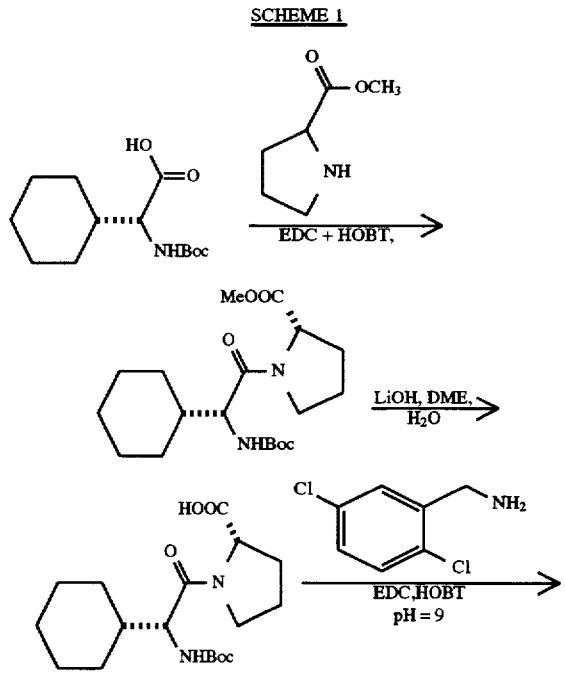

-continued
SCHEME 1

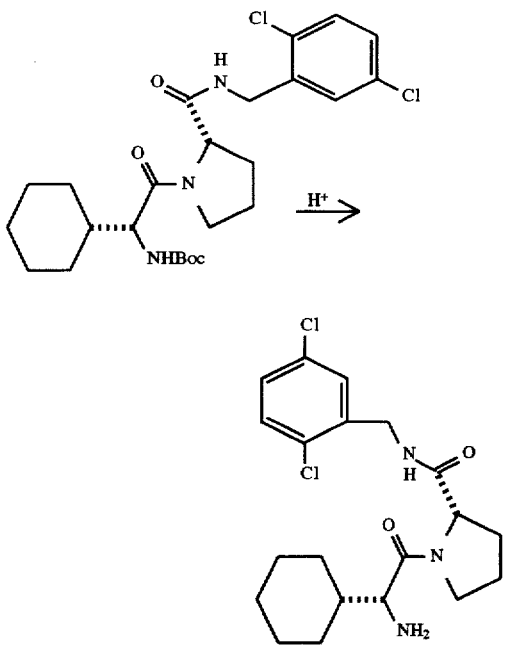

A method for synthesizing compounds illustrated in tables 2 and 3 is to react a free amino containing compound with an alkylating agent such as t-butyl-bromoacetate. The resulting compound is treated with acid to form an acid, and the resultant acid is coupled to the desired amine under standard coupling conditions. If the product has a protecting group, this is conveniently removed with acid (for acid lable groups).

SCHEME 2

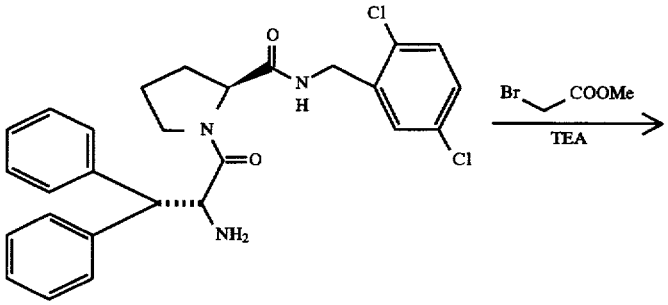

-continued
SCHEME 2

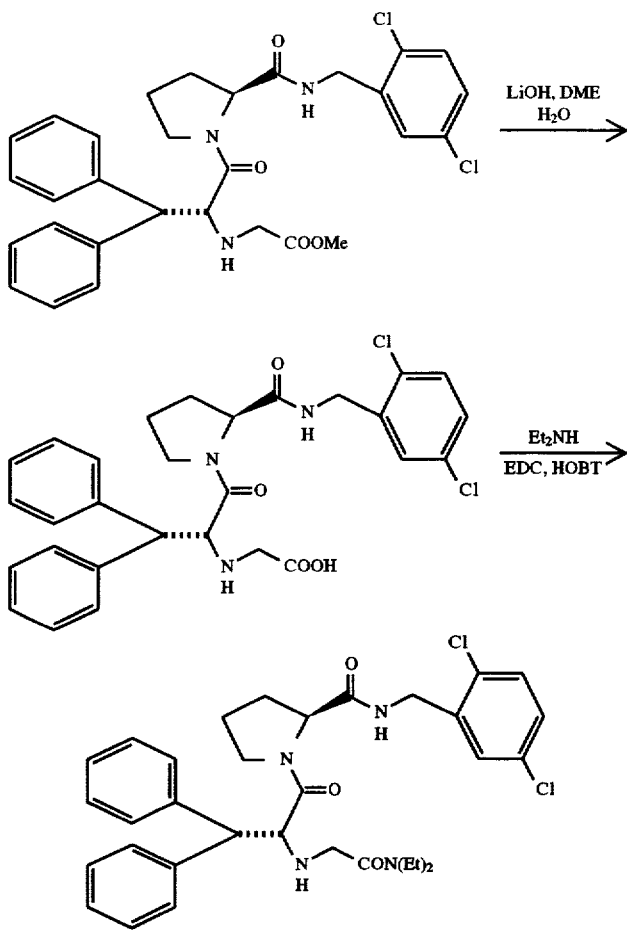

An alternate method for functionalizing the amine group is illustrated in Scheme 3. An amine, such as that from Example 1, treated with an aldehyde and a reducing agent such as sodium triacetoxyborohydride to give the desired product.

SCHEME 3

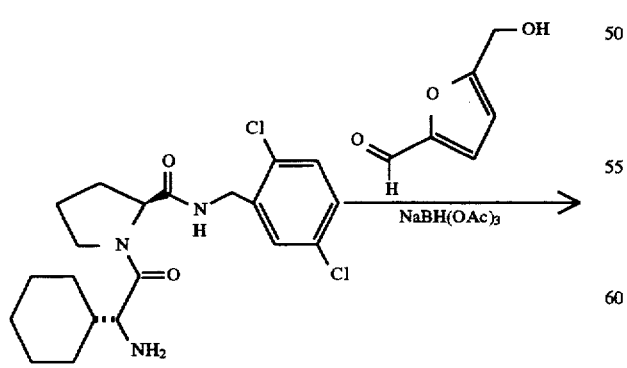

-continued
SCHEME 3

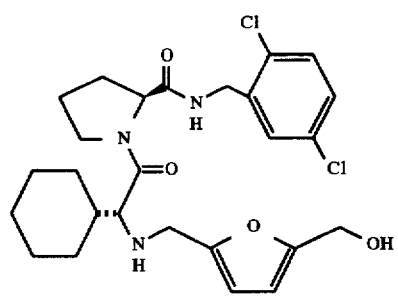

β-Aminoalkylsulfonamide containing compounds are synthesized by reacting an amino compound with a sulfonylating reagent such as chloroethyl sulfonyl chloride and a base such as triethylamine. The product is reacted with a primary or secondary amine to give the product. In some cases the amine contains a protecting group which is removed with acid.

5,798,377
17
SCHEME 4
18
-continued
SCHEME 4
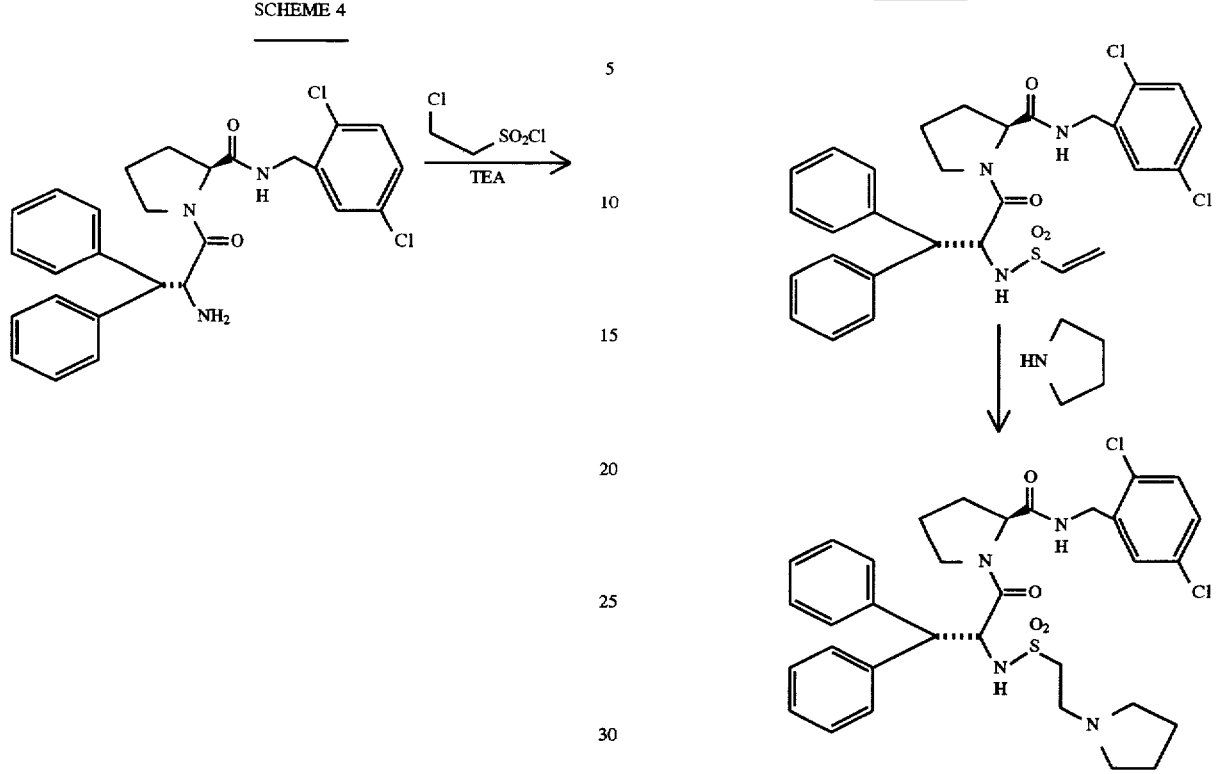
SCHEME 5
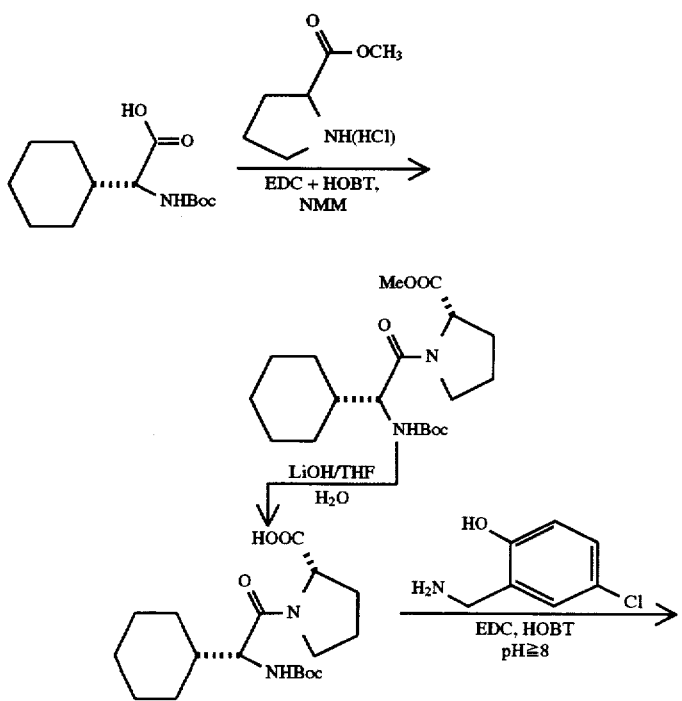

-continued
SCHEME 5
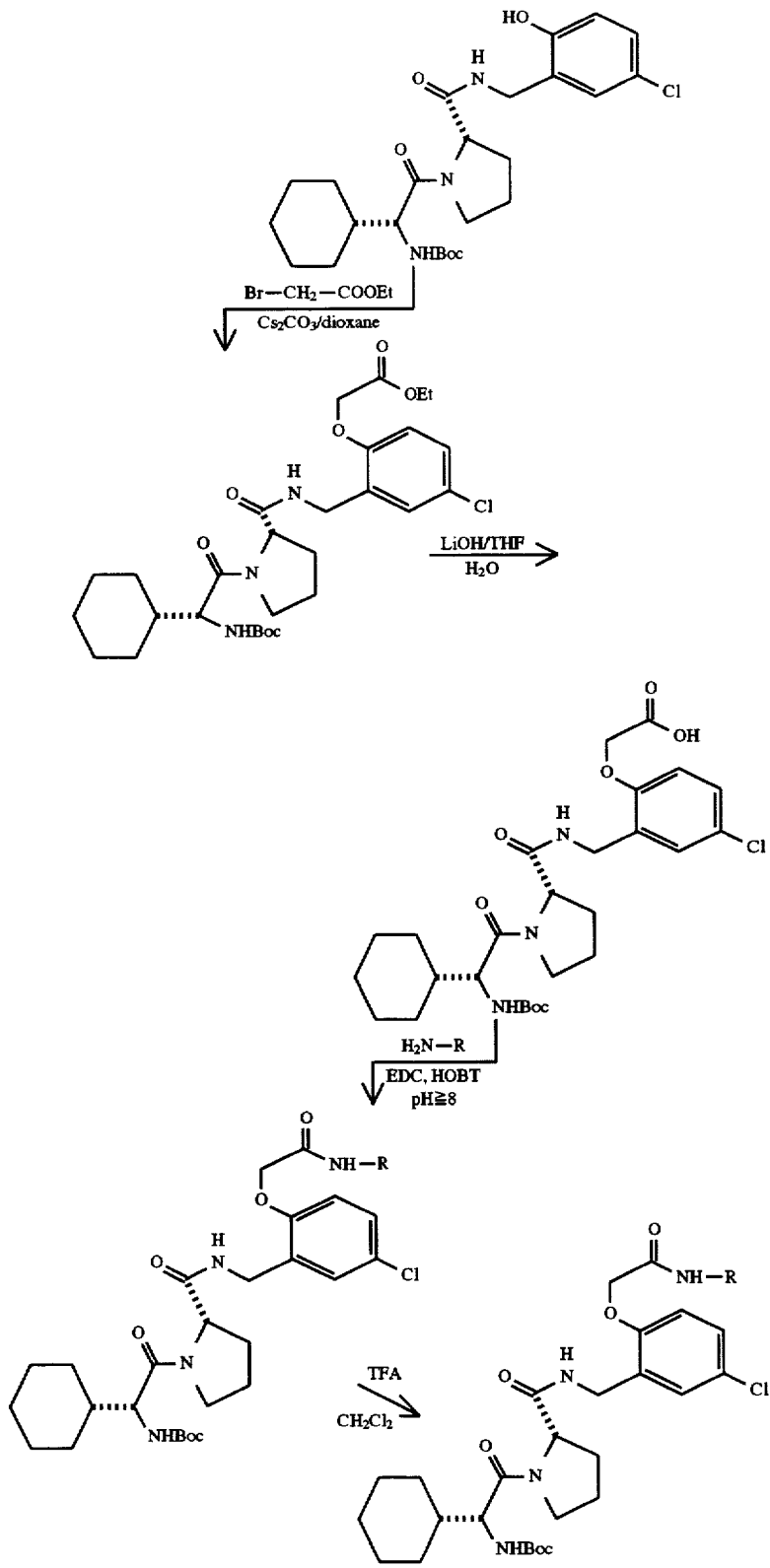

R represents, for example, hydrogen, $C_{1-4}$ alkyl, $C_{1-4}$ cycloalkyl or $CH_2CF_3$.

EXAMPLE 1

Preparation of D-β,β-diphenylala-Pro-N-(2,5-dichlorophenyl)methyl amide (1-1)

A solution of 418.00 mg (0.95 mmol) of Boc-(D)-β,β-diphenylala-ProOH, 168.00 mg (0.95 mmol) of 2,5-dichlorobenzylamine, 201.00 mg (1.05 mmol) of EDC, 142.00 mg (1.05 mmol) of HOBT, and 146.00 ml (1.05 mmol) of triethylamine in 8 ml anh. DMF was stirred at room temp. in an argon atmosphere for 18 h. The reaction was diluted with three times its volume of aq. 10% citric acid solution, and the resulting suspension was stirred vigorously for 45 min. The suspension was filtered, and the solid product dried in vacuo over anh. $P_2O_5$ to give 540 mg of the intermediate coupling product. The solid was dissolved in a minimum of EtOAc with a small amt. of $CHCl_3$ added to aid dissolution. The solution was cooled to $-10°$ C., and was bubbled with HCl gas for approx. five minutes. The solution was stirred at this temp. for twenty additional minutes, and was removed from the cooling bath. The solution was purged with argon, and a white amorph. solid precipitate resulted. Filtration and drying provided 1-1 as a white powder. Anal.$(C_{27}H_{27}N_3O_2Cl_2.HCl.0.35\ H_2O.0.50\ CHCl_3)$. CHN. High res. MS: theo., 496.15585; obs., 496.15652.

EXAMPLE 2

Preparation of D-β,β-diphenylala-Pro-N-(2-hydroxy-5-methyl)-benzylamide (2-1)

A solution of 96 mg (0.22 mmol) of Boc-D-diphenylala-Pro-OH and 40 mg (0.20 mmol) of 2-hydroxy-5-ethyl benzylamine hydrochloride in 15 ml of DMF was treated with 37 mg (0.24 mmol) of HOBT-$H_2O$ and N-methyl morpholine (pH 8 moistened pH 5–10 paper) followed by 50 mg of EDC (0.26 mmol). After stirring overnight, the reaction mixture was evaporated to dryness, the residue partitioned with EtOAc/dilute $NaHCO_3$; the organic layer washed with $H_2O$, dilute $NaHCO_3$, sat'd. NaCl; solvent was removed to afford crude intermediate. Approx. 3 ml of 100% trifluoroacetic acid was added to the residue, the solution set 15 min; the TFA was evaporated in vacuo and replaced with $CH_3CN$—$CH_3OH$—$H_2O$ (1:1:3), followed by preparative HPLC to afford, after lyophilization of fractions, 2-1. FAB-MS m/c 472 (M+H); HPLC>99%.

EXAMPLE 3

Preparation of D-β,β-diphenylala-Pro-N-(2,5-dimethoxy)-benzylamide (3-1)

A solution of 242 mg (0.55 mmol) of BOC-D-diphenylala-Pro-OH and 84 mg (0.50 mmol) of 2,5-dimethoxy benzylamine in 20 ml of DMF was treated with 92 mg (0.80 mmol) of HOBT, N-methylmorpholine, and 125 mg (0.65 mmol) of EDC as in Example 2. Standard workup afforded crude intermediate which treated with 5 ml of 100% TFA to remove the BOC group as in Example 2. Preparative HPLC afforded 170 mg of the desired product as the TFA salt, which was converted to the HCl salt. (HCl/EtOAc) to afford 3-1: FAB-MS m/e 488 (M+H), HPLC ca. 90%.

EXAMPLE 4

Preparation of N-carboxymethyl-D-β,β-diphenylala-Pro-N-(2,5-dimethoxy)-benzylamide (4-1)

A solution of 40 mg (0.082 mmol) of 3-1 and 16 mg of t-butyl bromoacetate with 22 ml (1.5 equiv.) of DIEA in 0.5 ml of DMF was stirred 20 min at 25°; followed by an additional equal amount of the latter two reagents, the reaction was complete in 48 hrs. After dilution with EtOAc, extractive workup afforded 38 mg of glassy solid intermediate. Approx. 3 ml of 100% TFA was used to remove the t-butyl ester, as in Example 2; the compound was purified by semi-preparative HPLC and the pooled fractions were evaporated and converted to the HCl salt. Filtration of the precipitated HCl salt from hexane.EtOAc gave 4-1. FAB-MS m/e 546 (M+H), HPLC ca. 95%.

EXAMPLE 5

Preparation of N-[2-(imidazolyl)-methyl]-D-β,β-diphenylala-Pro-N-(2,5-dichloro)-benzylamide (5-1)

A solution of 107 mg (0.20 mmol) of 1-1 in 2.0 ml of 0.24 M HOAc in 1,2-dichloroethane under $N_2$ was treated with 21 mg (0.21 mmol) of imidazole-2-carboxaldehyde, followed by 64 mg (0.30 mmol) of sodium triacetoxyborohydride. After 4 days an additional 0.5 equivalents more of the latter reagents were added, and the reaction was stirred an additional 2 days. The mixture was concentrated in vacuo to dryness, dissolved in ca. 1;3 HOAc—$H_2O$ and purified by preparative HPLC. Pooling of product containing fractions yielded, after lyophilization, 5-1: FAB-MS m/e 576 (M+H); HPLC ca. 95%.

EXAMPLE 6

Preparation of N-[4-(imidazolyl)-methyl]-D-β,β-diphenylala-Pro-N-(2,5-dichloro)-benzylamide (6-1)

As in Example 5 above, a solution of 214 mg (0.40 mmol) of 1-1 in 4.0 ml of 1,2-dichloroethane was treated with 59 mg (0.60 mmol) of imidazole-4-carboxaldehyde and 176 mg (0.80 mmol) of sodium triacetoxyborohydride. After 24 h, the solvent was concentrated in vacuo and the product purified by preparative HPLC as above to yield 141 mg of lyophilized 6-1: FAB-MS m/e 576 (M+H); HPLC 99%.

EXAMPLE 7

Preparation of N-[2-(5-hydroxymethylfuryl)-methyl]D-β,β-diphenylala-Pro-N-(2,5-dichloro)-benzylamide (7-1)

As in Example 5 above, a solution of 204 mg (0.40 mmol) of 1-1 in 4.0 ml of 1,2-dichloroethane under $N_2$ was treated with 74 mg 0.60 mmol) of 5-hydroxymethyl-2-furaldehyde and 164 mg (0.80 mmol) with sodium triacetoxyborohydride. After 24 hr the solvent was concentrated in vacuo and the product purified by preparative HPLC as above to yield 7-1: FAB-MS m/e 606 (M+H); HPLC 99%.

EXAMPLE 8

Preparation of N-[2-(5-dimethylaminofuryl)-methyl]-D-β,β-diphenylala-Pro-N-(2,5-dichloro)-benzylamide (8-1)

As in Example 5 above, a solution of 206 mg (0.40 mmol) of 1-1 in 4.0 ml of 1,2-dichloroethane under $N_2$ was treated with 86 mg (0.60 mmol) of 5-dimethylamino-2-furaldehyde and 170 mg (0.80 mmol) of sodium triacetoxyborohydride. After 24 hr the solvent was concentrated in vacuo and the product purified by preparative HPLC as above to yield 8-1: FAB-MS m/e 619 (M+H); HPLC>99%.

EXAMPLE 9

Preparation of N-(imino-aminomethyl)-methyl-D-β,β-diphenylala-Pro-N-(2,5-dichloro)-benzylamide (9-1)

A solution of 20 mg of 1-1 in 2.0 ml of DMF was treated with 11 mg of chloroacetamidine hydrochloride, followed by 2 drops of diisopropyl ethylamine. The mixture was heated at 50°–60° for 2 days; the solvent was evaporated in vacuo and the residue in $H_2O$/5% acetonitrile was processed by preparative HPLC to yield, after lyophilization, 9-1: FAB-MS m/e 552 (M+H); HPLC ca. 88%.

EXAMPLE 10
Preparation of D-cyclohexylglycyl-Pro-N-(2,5-dichloro)-benzylamide (10-1)

A solution of 1.00 g (3.89 mmol) of Boc-D-cyclohexyl glycine and 1.26 g (4.08 mmol) of (H)-prolyl-2,5-dichlorobenzylamide hydrochloride in 90 ml of DMF was treated with 0.71 g (4.67 mmol) of $HOBt.H_2O$ and N-methyl morpholine (pH 8); then 0.97 g (5.06 mmol) of EDC, followed by stirring 5 hr. The solution was concentrated in vacuo to a volume of ca. 20 ml, followed by partition with EtOAc/dilute $NaHCO_3$ and extractive workup as in Example 2 to give crude intermediate, which was purified by chromatography on silica gel, eluting with 1:1 EtOAc/hexane, to give 1.87 g (94% yield of coupled intermediate). The above sample in approx. 50 ml of EtOAc was saturated with HCl gas at $-10°$, set 60 min at $0°-20°$, followed by purging with $N_2$, as precipitate slowly formed. The solid was filtered and washed with ether, drying in vacuo to give 10-1: FAB-MS m/3 413 (M+H); HPLC 97%.

EXAMPLE 11
Preparation of N-carboxymethyl-D-cyclohexylglycyl-Pro-N-(2,5-dichloro)-benzylamide (11-1)

A solution of 289 mg (0.70 mmol) of 10-1 and 0.23 ml (0.28 g, 1.44 mmol) of t-butyl bromoacetate with 0.24 ml of DIEA in 5.0 ml of DMF, was stirred at 25° for 2 days. The solvent was removed in vacuo, the residue partitioned with EtOAc/dilute $NaHCO_3$, and the organic layer was washed with saturated NaCl and dried over $Na_2SO_4$. Solvent removal afforded 390 mg of crude intermediate, HPLC 95%. A solution of 87 mg of the above intermediate in 10 ml of EtOAc/$CH_2Cl_2$ (4/1) was saturated with HCl at $-10°$, set 30 min; then purged with $N_2$, and the solution concentrated under reduced pressure until appearance of solid. Precipitation was completed by addition of ether, and product was isolated by filtration, washing with ether, and drying in vacuo to give 11-1: FAB-MS m/e 480 (M+H); HPLC ca. 90%.

EXAMPLE 12
Preparation of N-((1-piperazinyl)-carboxy)-methyl-D-cyclohexylglycyl-Pro-N-(2,5-dichloro)-benzylamide (12-1)

A solution of 80 mg (0.16 mmol) of 11-1 and 36 mg (0.19 mmol) of t-BOC-1,4-piperazine in 2.0 ml of DMF was treated with 32 mg (0.21 mmol) of $HOBt.H_2O$ and N-methyl morpholine (pH 8); then 43 mg (0.22 mmol) of EDC was added, followed by stirring at 25° for 20 hr. The solvent was evaporated in vacuo and the residue partitioned with EtOAc/dilute $NaHCO_3$, washing with 2 portions of saturated NaCl, and dried over $Na_2SO_4$. Removal of solvent afforded 100 mg of crude intermediate. To the above sample was added 5.0 ml of TFA; let stir for 30 min, the TFA was evaporated under reduced pressure and the product was purified to give lyophilized 12-1; FAB-MS m/e 538 (M+H); HPLC 97%.

EXAMPLE 13
Preparation of D-β,β-diphenylala-Pro-N-(2,5-dimethylbenzyl)amide (13-1)

In a similar manner as in Example 1 but substituting 2,5-dimethylbenzylamine for 2,5-dichlorobenzylamine, 13-1.

EXAMPLE 14
Preparation of N-Phenylmethanesulfonyl-D-β,β-diphenylala-Pro-N-(2,5-dimethylbenzyl)amide (14-1)

D-β,β-diphenylala-L-Pro-N-(2,5-dimethylbenzyl)amide hydrochloride is reacted with hexamethyldisilazane (0.10 ml per 32 mg hydrochloride) in dry acetonitrile for 5 min at reflux. The mixture is cooled 30 min at room temperature and treated with phenylmethanesulfonyl chloride (50 mg). After 15 min at room temperature the mixture is diluted with $CH_2Cl_2$. The $CH_2Cl_2$ solution is washed with water, dried ($Na_2SO_4$) filtered and concentrated in vacuo. Chromatography on activity III neutral alumina gave 14-1. $M^+H^+/e$ 610 (calc'd for ($C_{36}H_{39}N_3O_4S$)=609.794.

EXAMPLE 15
Preparation of N-(4-pyridylmethanesulfonyl)-D-β,β-diphenylala-Pro-N-(2,5-dichlorobenzyl)amid (15-1)

In a similar manner 1-1 is reacted with 43 mg 4-pyridylmethanesulfonyl chloride (trifluoromethanesulfonic acid salt) and hexamethyldisilazane. Similar workup and preparative HPLC gave lyophilized fractions of the title compound as the trifluoroacetic acid salt. This is treated with HCl(g) in ethyl acetate to give the crystalline hydrochloride of 15-1; high resolution MS ($M^+H^+/e$)=651.605 ($C_{33}H_{32}Cl_2N_4O_4S^+H^+$).

EXAMPLE 16
Preparation of N-[(N,N-diethylcarboxamido)methyl]-D-β,β-diphenyl-ala-Pro-N-(2,5-dichloro)-benzylamide (16-1)

A solution of 100.00 mg (0.19 mmol) of 1-1, 41.00 mg (0.21 mmol) of alpha-bromo-(N,N-diethyl)acetamide, and 75.00 ml (0.42 mmol) of diisopropylethylamine in 1 ml anh. DMF was stirred at 50° C. in an argon atmosphere for 4 h. The solution was further stirred at room temp. for 48 h, and was concentrated in vacuo to give a tan oil. The crude oil was purified via reverse phase prep LC, and the pure product fractions combined and lyophilized. Lyophilization provided 16-1 as a fluffy white amorphous solid. Anal. ($C_{33}H_{38}N_4O_3$ $Cl_2$.2.00 TFA.1.00 $H_2O$), CHN. Mass Spec.: M+=609.

EXAMPLE 17
Preparation of N-[(4-methylpiperazine)carboxamidomethyl]-D-β,β-diphenylala-Pro-N-(2,5-dichloro)-benzylamide (17-1)

A solution of 38.00 mg (0.06 mmol) of N-carboxymethyl-D-β,β-diphenylala-Pro-N-(2,5-dichloro)-benzylamide, 7.00 ml (0.06 mmol) of 4-methyl piperazine, 1.00 mg (1.10 mmol) of EDC, 10.00 mg (1.10 mmol) of HOBT, and 20.00 ml (2.20 mmol) of triethylamine in 1 ml of anh. DMF was stirred for 18 h in an argon atm. The reaction was concentrated in vacuo to give a clear oil, which was purified via reverse phase prep LC. Pure product fractions were combined and lyophilized to provide 17-1 as an amorphous white powder. Anal.($C_{34}H_{39}N_5O_3Cl_2$.2.15 TFA.2.20 $H_2O$), CHN. Mass Spec.: M+=636.

EXAMPLE 18
Preparation of D-β,β-diphenylala-Pro-N-(2-hydroxy-5-chloro)-benzylamide (18-1)

A solution of 278.00 mg (0.64 mmol) of Boc-D-β,β-diphenylala-ProOH, 100.00 mg (0.64 mmol) of 2-hydroxy-5-chlorobenzylamine, 136.00 mg (0.71 mmol) of EDC, 96.00 mg (0.71 mmol) of HOBT, and 99.00 ml (0.71 mmol) of triethylamine in 2 ml anh. DMF was stirred in an argon atm. for 18 h. The reaction was diluted with aq. 10% citric acid, and the resulting suspension was stirred vigorously for 45 min. The suspension was filtered, and the recovered white solid dried in vacuo. The solid was dissolved in a minimum of EtOAc, and the solution was cooled to $-10°$ C. The solution was bubbled with HCl gas for approx. five minutes, and was stirred for an additional 30 min. The reaction was removed from the cooling bath, and was purged with argon. The solution was concentrated in vacuo to provide a clear oil. The oil was purified via reverse phase prep LC, and the pure product fractions combined and lyophilized to give 18-1 as a fluffy white amorphous powder. Anal. ($C_{27}H_{28}N_3O_3Cl.1.30$ TFA.0.55 $H_2O$). CHN. High Res. MS: theo.=478.18975, obs.=478.18940.

EXAMPLE 19
Preparation of N-|(N,N-diethylcarboxamido)methyl|-D-β, β-diphenyl-ala-Pro-N-(3-chloro)-benzylamide (19-1)

A solution of 150.00 mg (0.30 mmol) of D-β,β-diphenylala-Pro-N-(3-chloro)-benzylamide HCl (prepared from Boc-(D)-Dip-ProOH and 3-chlorobenzylamine via a procedure analogous to that described in Example 1), 64.00 mg (0.33 mmol) of alpha-bromo-N,N-diethylacetamide, and 105.00 ml (0.60 mmol) of triethylamine in 1 ml of anh. DMF was stirred at room temp. in an argon atm. for 18 h. The reaction was concentrated in vacuo to give a brown oil. The crude oil was purified by reverse phase prep LC, and the pure product fractions combined and lyophilized to give 19-1 as a tacky white amorphous powder. Anal. ($C_{33}H_{39}N_4O_3Cl$ . 1.65 TFA . 0.10 $H_2O$), CHN. Mass Spec.: M+=575.

EXAMPLE 20
Preparation of α-(R)-amino-α-(3,4-methylenedioxybenzyl) acetyl-Pro-N-(2,5-dichloro)-benzylamide (20-1)

A solution of 100.00 mg (90.30 mmol) of α-(R)-azido-α-(3,4-methylenedioxybenzyl)acetyl-ProOH, 53.00 mg (0.30 mmol) of 2,5-dichlorobenzylamine, 63.00 mg (0.33 mmol) of EDC, 45.00 mg(0.33 mmol) of HOBT, and 47.00 ml (0.33 mmol) of triethylamine in 1 ml of anh. DMF was stirred at room temp. in an argon atm. for 18 h. The reaction was diluted with 3 times its volume of aq. 10% citric acid, and the solution stirred for approx. 10 min. The mixture was extracted with 2×25 ml of EtOAc, and the combined extracts washed with water and brine and dried over anh. $MgSO_4$. Concentration provided a foam, which was purified via gravity column chromatography over silica gel with 2.5% $MeOH/CHCl_3$. Concentration of the pure fractions provided 120 mg of coupling product as a white foam. The coupling product (120.00 mg/0.27 mmol) was dissolved in 3 ml of ThF to which was added 50 ml of $H_2O$. The solution was treated with 71.00 mg (0.27 mmol) of triphenylphosphine, and the resulting solution stirred at 55° C. for 18 h. The reaction was concentrated in vacuo to a clear oil, which was purified via reverse phase prep LC. The pure product fractions were combined and lyophilized to provide 20-1 as a tacky white amorphous powder. Anal. ($C_{22}H_{21}N_3O_4Cl_2$.1.05 TFA.1.00 $H_2O$), CHN. Mass spec.: M+=464.

EXAMPLE 21
Preparation of D,L-(3,4-methylenedioxy)phenylglycine-Pro-N-(2,5-dichloro)-benzylamide (21-1)

A solution of 100.00 mg (0.34 mmol) of Boc-D,L-(3,4-methylenedioxy)phenylglycine, 105.00 mg (0.34 mmol) of 2,5-dichlorlbenzylamine, 73.00 mg (0.38 mmol) of EDC, 51.00 mg (0.38 mmol) of HOBT, and 105.00 ml (0.75 mmol) of triethylamine in 2 ml of anh. DMF was stirred for 18 h in an argon atmosphere. The reaction was diluted with 4 times its volume of aq. 10% citric acid, and the resulting suspension stirred vigorously for approx. 45 min. The suspension was filtered to give a white solid which was dried in vacuo over $P_2O_5$ to give 185 mg of crude coupling product. The product from above was dissolved in a min. of EtOAc, and the solution cooled to -10C. The cold solution was bubbled with HCl gas for approx. 5 min., and was stirred in the cold for an additional 20 min. The reaction was removed from the bath, and was purged with argon. A white precip. resulted, which was isolated via filtration. The solid became extremely tacky on exposure to the air, and was redissolved in EtOAc and dried over anh. $MgSO_4$. The solution was concentrated to an off-white oil/solid. The crude product was purified via reverse phase prep LC, and the pure product fractions combined and lyophilized. Lyophilization provided 21-1 as a fluffy white amorphous powder which was determined by HPLC to be a 1:1 mixture of diastereomers at the phenylglycine center. Anal.($C_{21}H_{21}N_3O_4Cl_2$.1.30 TFA.0.10 $H_2O$), CHN. Mass Spec.: M+=450.

EXAMPLE 22
Preparation of N-|(N,N-diethylcarboxamido)methyl|-(D)-cyclo-hexyliglycine-Pro-N-(2,5-dichloro)-benzylamide (22-1)

A solution of 50.00 mg (0.11 mmol) of D-cyclohexyl-glycine-Pro-N-(2,5-dichloro)-benzylamide HCl, 21.40 mg (0.11 mmol) of alpha-bromo-N,N-diethylacetamide, and 38.20 ml (0.22 mmol) of diisopropylethylamine in 1 ml anh. DMF was stirred in an argon atm. for 18 h. HPLC indicated that the reaction was only approx. 50% complete, so an additional 0.50 equivatents of the bromide was added, and the reaction was warmed to 60° C. for approx. 4 h. The reaction was concentrated in vacuo, and the crude brown oil product purified via reverse phase prep LC. Pure product fractions were combined and lyophilized to provide 22-1 as a tacky white amorphous powder. Anal. ($C_{26}H_{38}N_4O_3Cl_2$.1.65 TFA.0.65 $H_2O$), CHN. Mass Spec.: M+=525.

EXAMPLE 23
Preparation of D-cyclohexylglycine-homopro-N-(2,5-dichloro)-benzylamide (23-1)

A solution of 199.00 mg (0.77 mmol) of Boc-D-cyclohexyl-glycine, 250.00 mg (0.77 mmol) of proline-N-(2,5-dichloro)-benzylamide, 163.00 mg (0.85 mmol) of EDC, 115.00 mg (0.85 mmol) of HOBT, and 237.00 ml (1.70 mmol) of triethylamine in 5 ml of anh. DMF was stirred for 18 h in an argon atmosphere. The reaction was diluted with 3 times its volume of aq. 10% citric acid, and the resulting suspension stirred vigorously at room temp. for approx. 90 min. The suspension was filtered and the white solid dried in vacuo to provide 321 mg of the crude coupling product. The coupling product was dissolved in a min. of EtOAc, with a small amt. of $CHCl_3$ added to assist in solubilizing the material. The reaction was cooled to -10° C., and was bubbled with HCl gas for approx. 10 min. The cold solution was stirred for an additional 30 min., and the bath removed. The reaction was purged with argon, which provided a precipitate. Filtration and drying in vacuo provided 23-1 as a white crystalline solid, MP=198-201° C. Anal.($C_{21}H_{29}N_3O_2Cl_2$.HCl.1.05 $H_2$O.1.25 $CHCl_3$), CHN. Mass spec.: M+=426.

EXAMPLE 24
Preparation of N-(2-(1-pyrrolidinyl)-ethanesulfonyl)-amino-D-β,β-diphenylala-Pro-N-(2,5-dichlorobenzyl) amide (24-1)

A cooled suspension of 250.00 mg (0.43 mmol) 1-1 in dichloromethane is treated with three equivalents of triethylamine. The reaction is allowed to warm to room temperature over 18 hrs and is then concentrated and chromatographed via preparative TLC. The product is dissolved in acetonitrile which contains 2 equivalents of pyrrolidine. After stirring at room temperature for 48 hr, the reaction is concentrated and 24-1 is purified by preparative HPLC and isolated as the trifluoroacetic acid salt. Mass spec.: M+=657/659.

EXAMPLE 25

Resin based synthesis of thrombin inhibitors

Step A: Preparation of Pro(p-nitrobenzophenoneoxime-polystyrene) resin $pNO_2$ benzophenone-polystyrene oxime (0.5 mg/g, 1% cross-linked, 2.0 g) is slurried with BocProOH in 50 ml $CH_2Cl_2$ at room temperature and the suspension treated with 4 mL of a 0.5M solution of dicyclohexylcarbodiimide in $CH_2Cl_2$. The mixture is shaken 24 hr at room temperature then filtered. The resin is washed with alternating $CH_2Cl_2$ and ethylacetate and dried by suction.

The resin is suspended in a mixture of 15 ml trifluoroacetic acid and 30 ml of $CH_2Cl_2$ for 1.5 hr at room temperature and filtered. The resin is alternately steeped in $CH_2Cl_2$ and isopropanol then washed with isopropanol and excess $CH_2Cl_2$ and dried to constant weight under vacuum; 2.0 g.

Step B: Preparation of Boc-D-β,β-diphenylala-Pro(p-nitrobenzophenoneoxime-polystyrene) resin The resin from Step A is suspended in 20 ml $CH_2Cl_2$ containing 0.15 ml triethylamine and treated with a filtered solution of Boc D-β,β-diphenylalanine (1.02 g) in $CH_2Cl_2$ and 3 ml 0.5M dicyclohexylcarbodiimide (removes dicyclohexylurea). The mixture is shaken overnight at room temperature then filtered and washed alternating with isopropanol and $CH_2Cl_2$ and vacuum dried at 80° C. Amino acid analysis of the dried resin gave 214.8 mMol/g of Pro and an essentially equal amount of D-β,β-diphenylAla (after standard hydrolysis).

Step C: Release of dipeptide amides from resin and deblocking

A 10 µMol equivalent of the resin from Step B is shaken with 2 ml $CH_2Cl_2$ containing an amine, preferably a benzylamine (10–13 µMol or its HCl salt and 100 µMol of triethylamine) for 24 hr at room temperature. The mixture is filtered and the filtrate analyzed by HPLC to show the presence of Boc dipeptide amide and unreacted amine in constant ratio. The filtrates are concentrated under high vacuum and the residues treated with 10–20% trifluoroacetic acid in $CH_2Cl_2$ for 12 hr at room temperature. The mixtures are evaporated in a stream of nitrogen or under vacuum and the residues taken up in DMSO-water mixtures for bioassay as thrombin inhibitors.

EXAMPLE 26

Preparation of D-cyclohexylglycine-proline-N-(2-{O-carboxymethyl-N-ethylamide},5-chloro)-benzylamide (26-4)

Step A: Preparation of Boc-D-cyclohexylglycine-proline methyl ester (26-1)

A solution of 8.0 g (31.0 mmol) of Boc-D-cyclohexylglycine and 5.8 g (35 mmol) of proline methyl ester HCl salt in 100 ml of anh. DMF, mixed with 5.8 g (37.2 mmol) of HOBt with the pH adjusted to 7–8 with N-methylmorpholine (to moistened narrow-range pH paper), was treated with 7.9 g (40.3 mmol) of EDC and stirred for 18 hr in a nitrogen atmosphere. After 20 hr water (10 ml) was added, the solution concentrated in vacuo and partitioned with 400 ml EtOAc and 200 ml $H_2O$, washing with dil. $NaHCO_3$, $H_2O$, dil. $KHSO_4$, and twice with 50% satd NaCl, dried over $Na_2SO_4$ and concentrated under reduced pressure to give an oil. This crude material was chromatographed on 300 g silica gel in 1:1 (v/v) EtOAc/hexane to afford, after pooling of fractions, intermediary 26-1.

Step B: Preparation of Boc-D-cyclohexylglycine-proline (26-2)

26-1 (9.20 g) was dissolved in 90 ml of THF, adding 50 ml of $H_2O$, followed by 21 ml of 2.0N LiOH in portions over a period of 2 hr. The solution was let stir 20 hr and the reaction was worked up by addition of dil. $KHSO_4$ to neutrality, evacuation of solvent under reduced pressure to give a thick paste to which was added 200 ml of $H_2O$ in portions with stirring, followed by dil. $KHSO_4$ to acidity (pH<2). After stirring for 1 hr, the solid was isolated by filtration, washing with $H_2O$ twice, and drying in vacuo to give 6.45 g (72% yield overall) of intermediary Boc-D-cyclohexylglycine-proline. Evaporation of the filtrate to a volume of <100 ml afforded 26-2.

Step C: Preparation of Boc-D-cyclohexylglycine-proline-N-(2-{O-carbethoxymethyl}-5-chloro)-benzylamide (26-3)

A solution of 405 mg (1.15 mmol) of 26-2 and 147 mg (0.94 mmol) of 2-hydroxy,5-chlorobenzylamine in 6 ml of anh. DMF, mixed with 191 mg (1.25 mmol) of HOBt with the pH adjusted to 7–8 with N-methylmorpholine (to moistened narrow-range pH paper), was treated with 255 mg (1.34 mmol) of EDC and stirred for 18 h in a nitrogen atmosphere. After 20 hr water (10 ml) was added, the solution concentrated in vacuo and partitioned with EtOAc and $H_2O$, washing with dil. $NaHCO_3$, $H_2O$, dil. $KHSO_4$, and twice with 50% satd NaCl, dried over $Na_2SO_4$ and concentrated under reduced pressure to give 502 mg of the crude 2-hydroxy,5-chlorobenzylamide.

A solution of this material in 20 ml of peroxide-free anh. dioxane was mixed with 0.18 ml (1.55 mmol) of ethyl bromoacetate and 0.54 g (1.66 mmol) of $Cs_2CO_3$ under a nitrogen atmosphere, stirring 20 hr at 250°. A second addition of 0.04 ml (0.34 mmol) of ethyl bromoacetate and 0.15 g (0.18 mmol) of $Cs_2CO_3$ brought the O-alkylation to completion, and the product was isolated by evaporation of solvent under reduced pressure, partitioning with EtOAc and $H_2O$, washing with dil. NaCl, drying over $Na_2SO_4$, and solvent removal to give 26-3.

Step D: Preparation of Boc-D-cyclohexylglycine-proline-N-(2-{O-ethylacetamido}-5-chloro)-benzylamide (26-4) 26-3 (1.04 g) was saponified in 30 ml of 50% THF/$H_2O$ with 0.8 ml of 2.0N LiOH for 20 hr, followed by addition of dil. $KHSO_4$ to neutrality, evaporation under reduced pressure to a gum, partitioning with EtOAc/dil. $KHSO_4$ and washing twice with dil. NaCl. After drying over $Na_2SO_4$, solvent removal afforded solid Boc-D-cyclohexylglycine-proline-N-(2-{O-carboxymethyl}-5-chloro)-benzylamide.

A solution of 91 mg (0.16 mmol) of the above acid and 35 mg (0.43 mmol) of ethylamine hydrochloride in 10 ml of anh. DMF, mixed with 37 mg (0.24 mmol) of HOBt with the pH adjusted to 7–8 with N-methylmorpholine (to moistened narrow-range pH paper), was treated with 58 mg (0.30 mmol) of EDC and stirred for 18 h in a nitrogen atmosphere. After 20 hr water (1 ml) was added, the solution concentrated in vacuo and partitioned with EtOAc and $H_2O$, washing with dil. $NaHCO_3$, $H_2O$, dil. $KHSO_4$, and twice with 50% satd NaCl, dried over $Na_2SO_4$ and concentrated under reduced pressure to give the crude Boc-protected ethyl amide.

This intermediate was dissolved in 4 ml of 50% (v/v) TFA/$CH_2Cl_2$ for 30 min., the solvent was removed under reduced pressure, and the product was purified by preparative HPLC (0.1% TFA-100% $H_2O$/$CH_3CN$ ->50% over 30 min.) to afford 26-4 as a white lyophilized powder. Anal. ($C_{24}H_{35}N_4O_4Cl$.1.30 TFA.0.15 $H_2O$), CHN. Mass spec.: M+=479.

The compounds shown in the tables below are exemplary compounds of the present invention. The range of Ki values associated with the specifically listed compounds is represented as follows:

+++<10 nM

++>10 nM and <500 nM

+>500 nM

TABLE I
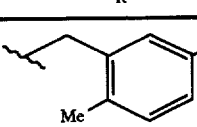
| X | R | $K_i$ Thrombin | $K_i$ Trypsin |
|---|---|---|---|
| H | 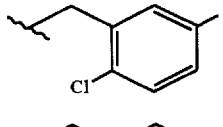 | ++ | + |
| H | 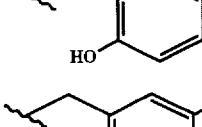 | +++ | + |
| H | 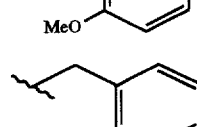 | ++ | + |
| H | 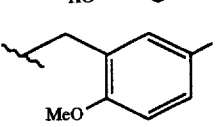 | ++ | + |
| H | 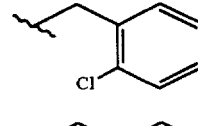 | ++ | + |
| $(Me)_2NCH_2CH_2OC(O)-$ | 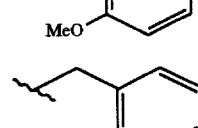 | ++ | + |
| $-CH_2COOH$ | 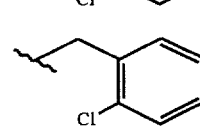 | ++ | + |
| 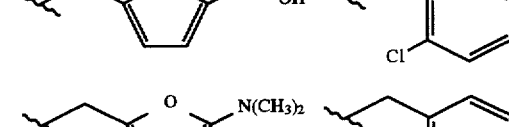 | 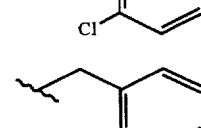 | ++ | + |
| 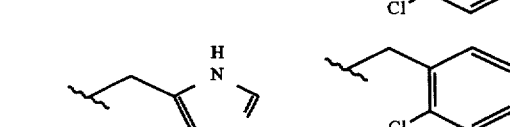 | 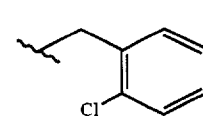 | ++ | + |
| 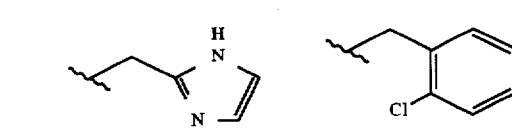 |  | ++ | + |

TABLE I-continued

| X | R | K_i Thrombin | K_i Trypsin |
|---|---|---|---|
| HOCH$_2$CH$_2$— | 2,5-dichlorobenzyl | ++ | + |
| 4-methylpiperazinyl-CO-CH$_2$-CH(~)- | 2,5-dichlorobenzyl | +++ | + |
| —CH$_2$CON(Et)$_2$ | 2,5-dichlorobenzyl | ++ | + |
| —CH$_2$CON(Et)$_2$ | 2,5-dichlorobenzyl | +++ | + |
| pyridin-4-yl-CH$_2$-SO$_2$— | 2,5-dichlorobenzyl | +++ | + |
| pyrrolidin-1-yl-CH$_2$CH$_2$-SO$_2$-CH$_3$ | 2,5-dichlorobenzyl | +++ | + |
| 3-amino-pyrrolidin-1-yl-CH$_2$CH$_2$-SO$_2$-CH$_3$ | 2,5-dichlorobenzyl | +++ | + |
| H$_2$N-CH$_2$CH$_2$-NH-CH$_2$CH$_2$-SO$_2$-CH$_3$ | 2,5-dichlorobenzyl | +++ | + |
| —CH$_2$COOH | 2,5-dichlorobenzyl | ++ | + |

TABLE II

[Structure: pyrrolidine-2-carboxamide with N-(2,5-dichlorobenzyl) and N-R substituent on ring nitrogen]

| R | $K_i$ Thrombin | Trypsin |
|---|---|---|
| [3,4-methylenedioxyphenyl-CH₂-CH(NH₂)-CO-] | +++ | + |
| [phenyl-CH(NH₂)-CO-] | ++ | + |
| [4-OH-3-OMe-phenyl-CH(NH₂)-CO-] | ++ | + |
| [9-hydroxy-9-acetyl-fluorene] | ++ | + |

TABLE III

[Structure: pyrrolidine-2-carboxamide with N-(2,5-dichlorobenzyl) amide and N-[cyclohexyl-CH(NHR)-CO-] substituent]

| R | $K_i$ Thrombin | Trypsin |
|---|---|---|
| H | +++ | + |
| CH₂COOH | +++ | + |
| CH₂CON(Et)₂ | +++ | + |

TABLE III-continued

[Same core structure as above]

| R | $K_i$ Thrombin | Trypsin |
|---|---|---|
| [−CO−CH(CONHt-Bu)−CH₂−piperidine-NH−] acyl | ++ | + |
| [−CO−CH₂−CH₂−piperazine-NH] | +++ | + |

TABLE IV

[Structure: pyrrolidine-2-carboxamide with N-(2-(OCH₂COR)-5-chlorobenzyl) amide and N-[cyclohexyl-CH(NH₂)-CO-] substituent]

| R | $K_i$ Thrombin | Trypsin |
|---|---|---|
| −OEt | +++ | + |
| −OH | +++ | + |
| −NH−Et | +++ | + |
| −NH₂ | +++ | + |
| −NH(CH₂)₂OH | +++ | + |
| −NH−cyclopropyl | +++ | + |
| −N(azetidine-3-ol) | +++ | + |

TABLE IV-continued

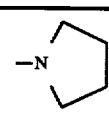

| R | K_i Thrombin | Trypsin |
|---|---|---|
| -N(pyrrolidine) | ++ | + |

TABLE V

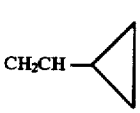

| $R_a$ | $R_b$ | D | K_i Thrombin | Trypsin |
|---|---|---|---|---|
| CH₃ | H | H | ++ | + |
| CH₃ | CH₃ | H | ++ | + |
| H | CH₂CH₃ | H | ++ | + |
| H | CH₂CH₂CH₃ | H | +++ | + |
| CH₂CH₃ | CH₂CH₃ | H | +++ | + |
| CH₂CH₃ | CH₂CH₃ | CH₃ | +++ | + |
| CH₂CH₂CH₃ | CH₂CH₂CH₃ | H | +++ | + |
| H | CH₂CH(CH₃)₂ | H | +++ | + |
| H | CH₂CH-(cyclopropyl) | H | +++ | + |

$K_i$ for thrombin range is the inhibition constant for the tested compound with human thrombin. $K_i$ for trypsin is the inhibition constant for the tested compound with human trypsin. Rate constants were determined using the following in vitro procedures.

In vitro assay for determining proteinase inhibition

Assays of human a-thrombin and human trypsin were performed at 25° C. in 0.05M TRIS buffer pH 7.4, 0.15M NaCl, 0.1% PEG. Trypsin assays also contained 1 mM CaCl₂.

In assays wherein rates of hydrolysis of a p-nitroanilide (pna) substrate were determined, a Thermomax 96-well plate reader was used to measure (at 405 nm) the time dependent appearance of p-nitroaniline. sar-PR-pna (sarcosine-Pro-Arg-p-nitroanilide) was used to assay human a-thrombin ($K_m$=125 μM) and human trypsin ($K_m$=59 μM). p-Nitroanilide substrate concentration was determined from measurements of absorbance at 342 nm using an extinction coefficient of 8270 cm⁻¹M⁻¹.

In certain studies with potent inhibitors ($K_i$<10 nM) where the degree of inhibition of thrombin was high, a more sensitive activity assay was employed. In this assay the rate of thrombin catalyzed hydrolysis of the fluorogenic substrate Z-GPR-afc (Cbz-Gly-Pro-Arg-7-amino-4-trifluoromethyl coumarin) ($K_m$=27 μM) was determined from the increase in fluorescence at 500 nm (excitation at 400 nm) associated with production of 7-amino4-trifluoromethyl coumarin. Concentrations of stock solutions of Z-GPR-afc were determined from measurements of absorbance at 380 nm of the 7-amino-4-trifluoromethyl coumarin produced upon complete hydrolysis of an aliquot of the stock solution by thrombin.

Activity assays were performed by diluting a stock solution of substrate at least tenfold to a final concentration ≤0.5 $K_m$ into a solution containing enzyme or enzyme equilibrated with inhibitor. Times required to achieve equilibration between enzyme and inhibitor were determined in control experiments. Initial velocities of product formation in the absence ($V_o$) or presence of inhibitor ($V_i$) were measured. Assuming competitive inhibition, and that unity is negligible compared $K_m$/[S], [I]/e, and [I]/e (where [S], [I], and e respectively represent the total concentrations, of substrate, inhibitor and enzyme), the equilibrium constant ($K_i$) for dissociation of the inhibitor from the enzyme can be obtained from the dependence of $V_o/V_i$ on [I] shown in equation 1.

$$V_o/V_i=1+[I]/K_i \quad (1)$$

The activities shown by this assay indicate that the compounds of the invention are therapeutically useful for treating various conditions in patients suffering from unstable angina, refractory angina, myocardial infarction, transient ischemic attacks, atrial fibrillation, thrombotic stroke, embolic stroke, deep vein thrombosis, disseminated intravascular coagulation, and reocclusion or restenosis of recanalized vessels.

Thrombin Inhibitors—Therapeutic Uses

Anticoagulant therapy is indicated for the treatment and prevention of a variety of thrombotic conditions, particularly coronary artery and cerebrovascular disease. Those experienced in this field are readily aware of the circumstances requiring anticoagulant therapy. The term "patient" used herein is taken to mean mammals such as primates, including humans, sheep, horses, cattle, pigs, dogs, cats, rats, and mice.

Thrombin inhibition is useful not only in the anticoagulant therapy of individuals having thrombotic conditions, but is useful whenever inhibition of blood coagulation is required such as to prevent coagulation of stored whole blood and to prevent coagulation in other biological samples for testing or storage. Thus, thrombin inhibitors can be added to or contacted with any medium containing or suspected of containing thrombin and in which it is desired that blood coagulation be inhibited, e.g. when contacting the mammal's blood with material selected from the group consisting of vascular grafts, stents, orthopedic prothesis, cardiac prosthesis, and extracorporeal circulation systems The thrombin inhibitors of the invention can be administered in such oral forms as tablets, capsules (each of which includes sustained release or timed release formulations), pills, powders, granules, elixers, tinctures, suspensions, syrups, and emulsions. Likewise, they may be administered in intravenous (bolus or infusion), intraperitoneal, subcutaneous, or intramuscular form, all using forms well known to those of ordinary skill in the pharmaceutical arts. An effective but non-toxic amount of the compound desired can be employed as an anti-aggregation agent. For treating ocular build up of fibrin, the compounds may be administered intraocularly or topically as well as orally or parenterally.

The thrombin inhibitors can be administered in the form of a depot injection or implant preparation which may be formulated in such a manner as to permit a sustained release of the active ingredient. The active ingredient can be compressed into pellets or small cylinders and implanted subcutaneously or intramuscularly as depot injections or implants. Implants may employ inert materials such as biodegradable polymers or synthetic silicones, for example, Silastic, silicone rubber or other polymers manufactured by the Dow-Corning Corporation.

The thrombin inhibitors can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The thrombin inhibitors may also be delivered by the use of monoclonal antibodies as individual carriers to which the compound molecules are coupled. The thrombin inhibitors may also be coupled with soluble polymers as targetable drug carriers. Such polymers can include polyvinlypyrrolidone, pyran copolymer, polyhydroxypropyl- methacrylamide-phenol, polyhydroxyethyl- aspartamide-phenol, or polyethyleneoxide-polylysine substituted with palmitoyl residues. Furthermore, the thrombin inhibitors may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels.

The dosage regimen utilizing the thrombin inhibitors is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Oral dosages of the thrombin inhibitors, when used for the indicated effects, will range between about 0.1 mg per kg of body weight per day (mg/kg/day) to about 100 mg/kg/day and preferably 1.0–100 mg/kg/day and most preferably 1–20 mg/kg/day. Intravenously, the most preferred doses will range from about 0.01 to about 10 mg/kg/minute during a constant rate infusion. Advantageously, the thrombin inhibitors may be administered in divided doses of two, three, or four times daily. Furthermore, they can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, or course, be continuous rather than intermittent throughout the dosage regime.

For example, oral tablets can be prepared which contain an amount of active compound of between 25 and 500 mg, typically between 200 and 250 mg. Typically, a patient in need of thrombin inhibitor compound, depending on weight and metabolism of the patient, would be administered between about 100 and 1000 mg active compound per day. For a patient requiring 1000 mg per day, two tablets containing 250 mg of active compound can be administered in the morning and two tablets containing 250 mg of active compound can again be administered in the evening. For a patient requiring 500 mg per day, one tablet containing 250 mg of active compound can be administered in the morning and one tablet containing 250 mg of active compound can again be administered in the evening.

The thrombin inhibitors are typically administered as active ingredients in admixture with suitable pharmaceutical diluents, excipients or carriers (collectively referred to herein as "carrier" materials) suitably selected with respect to the intended form of administration, that is, oral tablets, capsules, elixers, syrups and the like, and consistent with convention pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include starch, gelatin, natural sugars such as glucose or betalactose, corn-sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch methyl cellulose, agar, bentonite, xanthan gum and the like.

The thrombin inhibitors can also be co-administered with suitable anti-coagulation agents or thrombolytic agents such as plasminogen activators or streptokinase to achieve synergistic effects in the treatment of various ascular pathologies. For example, thrombin inhibitors enhance the efficiency of tissue plasminogen activator-mediated thrombolytic reperfusion. Thrombin inhibitors may be administered first following thrombus formation, and tissue plasminogen activator or other plasminogen activator is administered thereafter. They may also be combined with heparin, aspirin, or warfarin.

EXAMPLE 27

Tablet Preparation

Tablets containing 25.0, 50.0, and 100.0 mg, respectively, of the following active compounds are prepared as illustrated below:

N-[4-(imidazolyl)-methyl]-D-β,β-diphenylala-Pro-N-(2,5-dichloro)-benzylamide

N-[2-(5-hydroxymethylfuryl)-methyl]-D-β,β-diphenylala-Pro-N-(2,5-dichloro)-benzylamide N-[2-(5-dimethylaminofuryl)-methyl]-D-β,β-diphenylala-Pro-N-(2,5-dichloro)-benzylamide

| Ingredient | Amount-mg | | |
|---|---|---|---|
| Active Compound | 25.0 | 50.0 | 100.0 |
| Microcrystalline cellulose | 37.25 | 100.0 | 200.0 |
| Modified food corn starch | 37.25 | 4.25 | 8.5 |
| Magnesium stearate | 0.50 | 0.75 | 1.5 |

All of the active compound, cellulose, and a portion of the corn starch are mixed and granulated to 10% corn starch paste. The resulting granulation is sieved, dried and blended with the remainder of the corn starch and the magnesium stearate. The resulting granulation is then compressed into tablets containing 25.0, 50.0, and 100.0 mg, respectively, of active ingredient per tablet. EXAMPLE 28

An intravenous dosage form of the above-indicated active compound is prepared as follows:

| Active Compound | 0.5–10.0 mg |
|---|---|
| Sodium Citrate | 5–50 mg |
| Citric Acid | 1–15 mg |
| Sodium Chloride | 1–8 mg |
| Water for Injection (USP) | q.s. to 1 L |

Utilizing the above quantities, the active compound is dissolved at room temperature in a previously prepared solution of sodium chloride, citric acid, and sodium citrate in Water for Injection (USP, see page 1636 of United States Pharmacopeia/National Formulary for 1995, published by United States Pharmacopeial Convention, Inc., Rockville, Md., copyright 1994.

What is claimed is:

1. A compound having the following structure:

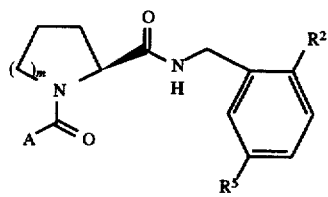

or a pharmaceutically acceptable salt thereof wherein

A is

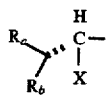

wherein $R_a$ and $R_b$ are independently selected from
  hydrogen,
  $C_{1-4}$ alkyl unsubstituted or substituted with $CH_3$ or $C_{3-7}$ cycloalkyl,
  aryl,
  substituted aryl with one or two substituents selected from
    $C_{1-4}$ alkyl,
    $C_{1-4}$ alkoxy,
    methylenedioxy,
    halogen or
    hydroxy,
  $C_{3-7}$ cycloalkyl, or
  $R_a$ and $R_b$, along with the carbon to which they are attached, form a $C_{3-7}$ cycloalkyl ring;

X is —$NHRC_c$, wherein, $R_c$ is
  hydrogen,
  —$CH_3$,
  —$(CH_2)_{1-3}CH_3$,
  —$(CH_2)_{2-4}OH$,
  —$(CH_2)_{1-3}COOH$,
  —$(CH_2)_{1-3}COOR^6$, where $R^6$ is $C_{1-4}$ alkyl,
  —$(CH_2)_{1-3}CONR^7R^8$,
    where $R^7$ and $R^8$ are independently hydrogen or $C_{1-4}$ alkyl,
  —$SO_2(CH_2)_{1-3}$aryl,
  —$(CH_2)_{1-3}NH_2$,
  $C_{3-7}$ cycloalkyl ring unsubstituted or substituted with —OH, —C(O)OH, or —C(O)OR$_d$, where $R_d$ is $C_{1-4}$ alkyl,

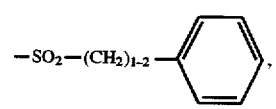

$R^2$ and $R^5$ are independently selected from
  hydrogen, provided that $R^2$ and $R^5$ are not both hydrogen,
  $C_{1-4}$ alkyl,
  $C_{1-4}$ alkoxy,
  halogen,
  —COOH,
  —OH,
  —COOR$^6$, where $R^6$ is $C_{1-4}$ alkyl,
  —CONR$^7R^8$, where $R^7$ and $R^8$ are independently hydrogen or $C_{1-4}$ alkyl,
  —OCH$_2$CO$_2$H,
  —OCH$_2$CO$_2$CH$_3$,
  —OCH$_2$CO$_2$(CH$_2$)$_{1-3}$CH$_3$,
  —O(CH$_2$)$_{1-3}$C(O)NR$^3R^4$, wherein $R^3$ and $R^4$ are independently hydrogen, $C_{1-4}$alkyl, $C_{3-7}$ cycloalkyl, or —CH$_2$CF$_3$,
  —(CH$_2$)$_{1-4}$OH,
  —NHC(O)CH$_3$,
  —NHC(O)CF$_3$,
  —NHSO$_2$CH$_3$, and
  —SO$_2$NH$_2$; and m is 1.

2. A compound of claim 1 having the following structure:

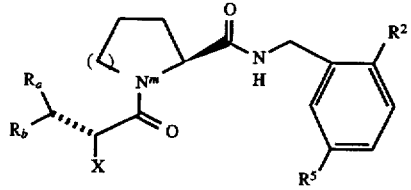

or a pharmaceutically acceptable salt thereof.

3. A compound of claim 2 having the following structure:

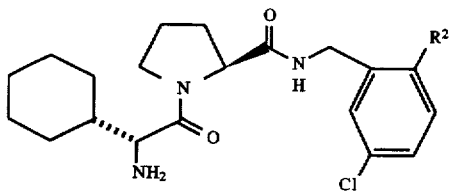

or a pharmaceutically acceptable salt thereof, wherein $R^2$ is —OCH$_2$C(O)NHR$^4$; and $R^4$ is —CH$_2$CH$_3$, cyclopropyl, or —CH$_2$CF$_3$.

4. A compound of claim 3 selected from the group consisting of:

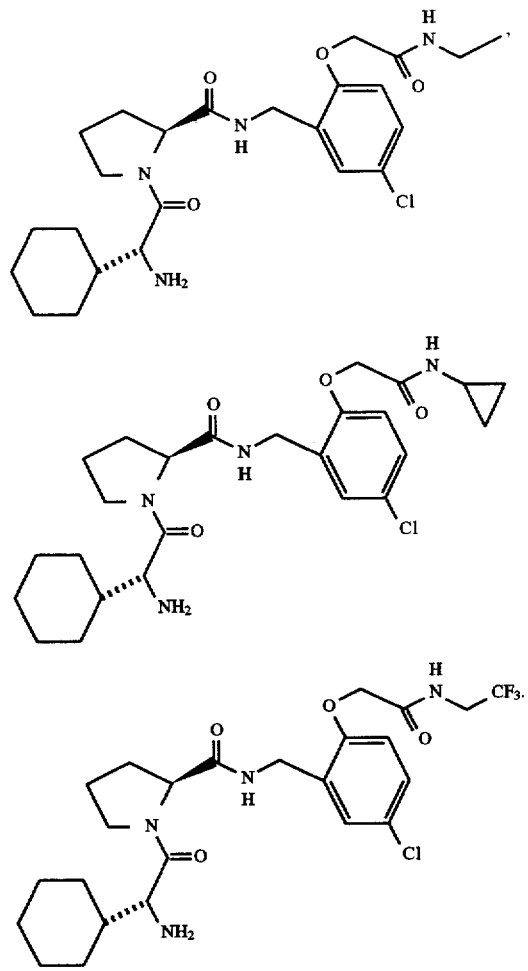

or a pharmaceutically acceptable salt thereof.

5. A compound of claim 1 having the following structure:

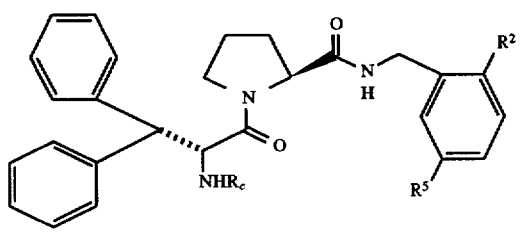

or a pharmaceutically acceptable salt thereof wherein $R^2$ and $R^5$ are independently selected from —OCH$_3$ and —CH$_3$; and $R_c$ is hydrogen or —SO$_2$CH$_2$C$_6$H$_5$.

6. A compound of claim 5 selected from the group consisting of:

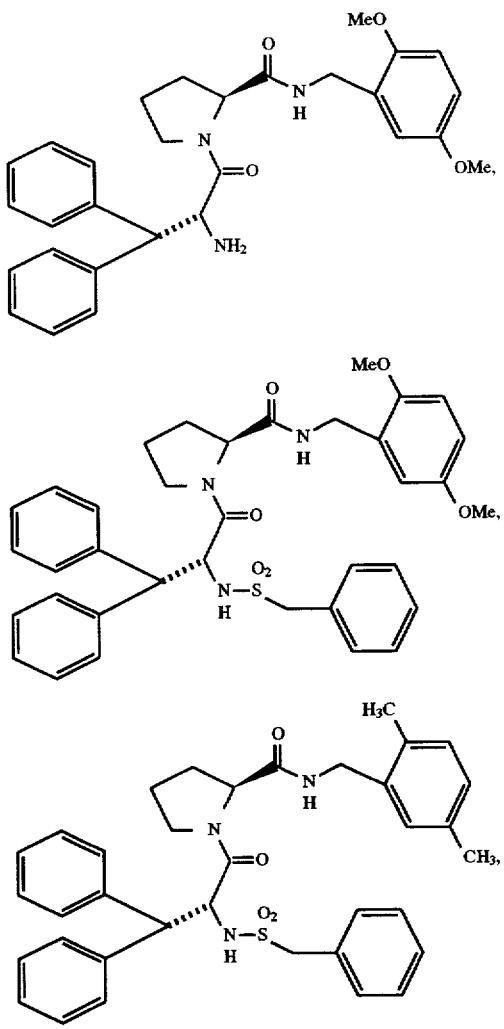

or a pharmaceutically acceptable salt thereof.

7. A compound of claim 1 having the following structure:

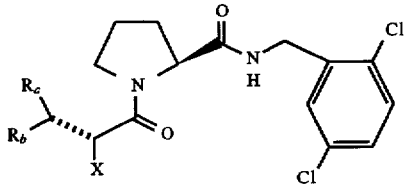

or a pharmaceutically acceptable salt thereof.

8. A compound of claim 7 having the following structure:

or a pharmaceutically acceptable salt thereof, wherein $R_c$ is hydrogen,

SO$_2$CH$_2$C$_6$H$_5$, or

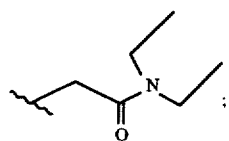

and

R$_a$ and R$_b$ are phenyl, or R$_a$ and R$_b$, along with the carbon to which they are attached, form cyclohexyl.

9. A compound of claim 8 selected from the group consisting of:

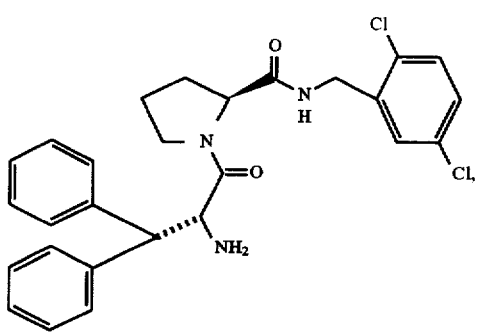

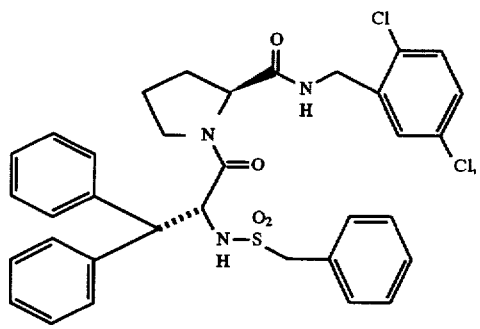

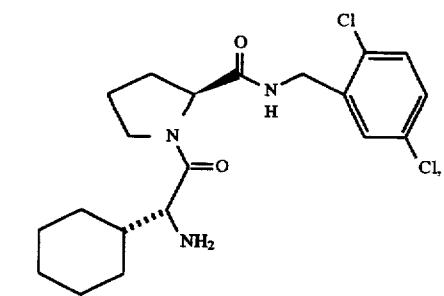

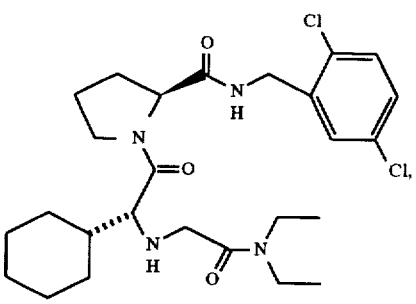

or a pharmaceutically acceptable salt thereof.

10. A composition for inhibiting thrombin in blood comprising an effective amount of a compound of claim 1 and a pharmaceutically acceptable carrier.

11. A composition for inhibiting thrombus formation in blood comprising an effective amount of a compound of claim 1 and a pharmaceutically acceptable carrier.

12. A method for inhibiting thrombin in blood in a mammal in need of said treatment comprising administering to the mammal an effective amount of a composition of claim 10.

13. A method for inhibiting thrombus formation in blood in a mammal in need of said treatment comprising administering to the mammal an effective amount of a composition of claim 11.

14. A method for inhibiting thrombin in stored blood comprising administering to the mammal a composition of claim 10.

15. A method for inhibiting thrombus formation in stored blood comprising administering to the mammal in need of said treatment an effective amount of a composition of claim 11.

16. A composition for inhibiting thrombus formation in blood comprising an effective amount of a compound of claim 1, a fibrinogen receptor antagonist, and a pharmaceutically acceptable carrier.

17. A method for inhibiting thrombus formation in blood in a mammal in need of said treatment comprising administering to the mammal an effective amount of a composition of claim 16.

* * * * *